US010118100B2

(12) United States Patent
Dugan

(10) Patent No.: US 10,118,100 B2
(45) Date of Patent: Nov. 6, 2018

(54) SYSTEMS AND METHODS FOR FITNESS AND VIDEO GAMES

(71) Applicant: Brian M. Dugan, Sleepy Hollow, NY (US)

(72) Inventor: Brian M. Dugan, Sleepy Hollow, NY (US)

(*) Notice: Subject to any disclaimer, the term of this patent is extended or adjusted under 35 U.S.C. 154(b) by 0 days.

(21) Appl. No.: 15/628,612

(22) Filed: Jun. 20, 2017

(65) Prior Publication Data
US 2017/0286641 A1 Oct. 5, 2017

Related U.S. Application Data

(63) Continuation of application No. 14/536,599, filed on Nov. 8, 2014, now Pat. No. 9,700,802, which is a
(Continued)

(51) Int. Cl.
A63F 13/79 (2014.01)
A63B 71/06 (2006.01)
A63F 13/816 (2014.01)
G06K 9/00 (2006.01)
G09B 19/00 (2006.01)
(Continued)

(52) U.S. Cl.
CPC .......... A63F 13/79 (2014.09); A63B 71/0622 (2013.01); A63F 13/816 (2014.09); G06K 9/00342 (2013.01); G09B 19/00 (2013.01); A63B 2230/00 (2013.01); A63F 13/812 (2014.09); A63F 2300/535 (2013.01); A63F 2300/5546 (2013.01); A63F 2300/5553 (2013.01); G06F 19/3481 (2013.01)

(58) Field of Classification Search
CPC ...... A63F 13/79; A63F 13/816; A63F 13/812; A63F 2300/5553; A63F 2300/5546; A63F 2300/535; A63B 71/0622; A63B 2300/00; G06K 9/00342; G09B 19/00; G06F 19/3481
See application file for complete search history.

(56) References Cited

U.S. PATENT DOCUMENTS 3,834,702 A 9/1974 Bliss
4,484,743 A 11/1984 Williams
(Continued)

FOREIGN PATENT DOCUMENTS

EP 1 292 217 B1 11/2005
EP 1 639 939 A1 3/2006
(Continued)

OTHER PUBLICATIONS

Busch, Fritz "Diabetes Institute Brings Dakota, New Ulm Together" Jun. 10, 2001. Ogden Newspapers, Inc.
(Continued)

Primary Examiner — Jasson Yoo
(74) Attorney, Agent, or Firm — Dugan & Dugan, PC

(57) ABSTRACT

In some aspects, an application is provided that is adapted to execute on at least a first mobile device. The application is adapted to (a) track information regarding a user of the mobile device; (b) create an avatar based on the tracked information; and (c) employ the avatar to provide preemptive warnings to assist in avoidance of unwanted behavior by the user. Numerous other aspects are provided.

20 Claims, 13 Drawing Sheets

Related U.S. Application Data continuation of application No. 13/456,196, filed on Apr. 25, 2012, now abandoned, which is a continuation-in-part of application No. 13/440,987, filed on Apr. 5, 2012, now Pat. No. 9,610,506, which is a continuation-in-part of application No. 13/433,285, filed on Mar. 28, 2012, now Pat. No. 9,533,228.

(60) Provisional application No. 61/478,913, filed on Apr. 25, 2011, provisional application No. 61/472,191, filed on Apr. 5, 2011, provisional application No. 61/468,444, filed on Mar. 28, 2011, provisional application No. 61/472,191, filed on Apr. 5, 2011.

(51) Int. Cl.
*G06F 19/00* (2018.01)
*A63F 13/812* (2014.01)

(56) References Cited

U.S. PATENT DOCUMENTS

| | | |
|---|---|---|
| 4,542,897 A | 9/1985 | Melton et al. |
| 4,735,410 A | 4/1988 | Nobuta |
| 4,817,938 A | 4/1989 | Nakao et al. |
| 4,858,930 A | 8/1989 | Sato |
| 4,976,435 A | 12/1990 | Shatford et al. |
| 5,001,632 A | 3/1991 | Hall-Tipping |
| 5,031,161 A | 7/1991 | Kendrick |
| 5,142,358 A | 8/1992 | Jason |
| RE34,728 E | 9/1994 | Hall-Tipping |
| 5,362,069 A | 11/1994 | Hall-Tipping |
| 5,377,100 A | 12/1994 | Pope et al. |
| 5,462,504 A | 10/1995 | Trulaske et al. |
| 5,515,865 A | 5/1996 | Scanlon |
| 5,527,239 A | 6/1996 | Abbondanza |
| 5,591,104 A | 1/1997 | Andrus et al. |
| 5,592,401 A | 1/1997 | Kramer |
| 5,624,316 A | 4/1997 | Roskowski et al. |
| 5,645,513 A | 7/1997 | Haydocy et al. |
| 5,667,459 A | 9/1997 | Su |
| 5,672,107 A | 9/1997 | Clayman |
| 5,702,323 A | 12/1997 | Poulton |
| 5,781,698 A | 7/1998 | Teller et al. |
| 5,885,156 A | 3/1999 | Toyohara et al. |
| 5,902,250 A | 5/1999 | Verrier et al. |
| 5,918,603 A | 7/1999 | Brown |
| 5,928,133 A | 7/1999 | Halyak |
| 5,947,868 A | 9/1999 | Dugan |
| 6,024,675 A | 2/2000 | Kashiwaguchi |
| 6,062,216 A | 5/2000 | Corn |
| 6,066,075 A | 5/2000 | Poulton |
| 6,152,856 A | 11/2000 | Studor et al. |
| 6,179,713 B1 | 1/2001 | James et al. |
| D439,981 S | 4/2001 | Kasabach et al. |
| 6,213,872 B1 | 4/2001 | Harada et al. |
| 6,244,988 B1 | 6/2001 | Delman |
| 6,251,010 B1 | 6/2001 | Tajiri et al. |
| 6,267,677 B1 | 7/2001 | Tajiri et al. |
| 6,302,789 B2 | 10/2001 | Harada et al. |
| D451,604 S | 12/2001 | Kasabach et al. |
| 6,347,993 B1 | 2/2002 | Kondo et al. |
| 6,354,940 B1 | 3/2002 | Itou et al. |
| 6,375,572 B1 | 4/2002 | Masuyama et al. |
| D460,971 S | 7/2002 | Sica et al. |
| 6,456,749 B1 | 9/2002 | Kasabach et al. |
| 6,482,092 B1 | 11/2002 | Tajiri et al. |
| 6,494,830 B1 | 12/2002 | Wessel |
| 6,513,160 B2 | 1/2003 | Dureau |
| 6,514,199 B1 | 2/2003 | Alessandri |
| 6,527,711 B1 | 3/2003 | Stivoric et al. |
| 6,579,231 B1 | 6/2003 | Phipps |
| 6,585,622 B1 | 7/2003 | Shum et al. |
| 6,595,858 B1 | 7/2003 | Tajiri et al. |
| 6,595,929 B2 | 7/2003 | Stivoric et al. |
| 6,605,038 B1 | 8/2003 | Teller et al. |
| 6,628,847 B1 | 9/2003 | Kasabach et al. |
| 6,641,482 B2 | 11/2003 | Masuyama et al. |
| 6,652,383 B1 | 11/2003 | Sonoda et al. |
| 6,705,972 B1 | 3/2004 | Takano et al. |
| 6,720,983 B1 | 4/2004 | Massaro et al. |
| 6,746,371 B1 | 6/2004 | Brown et al. |
| 6,758,746 B1 | 7/2004 | Hunter et al. |
| 6,786,825 B2 | 9/2004 | Kawazu |
| 6,796,927 B2 | 9/2004 | Toyama |
| 6,881,176 B2 | 4/2005 | Oishi et al. |
| 6,888,779 B2 | 5/2005 | Mollicone et al. |
| 6,902,513 B1 | 6/2005 | McClure |
| 6,966,837 B1 | 11/2005 | Best |
| 7,020,508 B2 | 3/2006 | Stivoric et al. |
| 7,041,049 B1 | 5/2006 | Raniere |
| 7,057,551 B1 | 6/2006 | Vogt |
| 7,068,860 B2 | 6/2006 | Kasabach et al. |
| 7,153,262 B2 | 12/2006 | Stivoric et al. |
| 7,261,690 B2 | 8/2007 | Teller et al. |
| 7,285,090 B2 | 10/2007 | Stivoric et al. |
| 7,302,398 B2* | 11/2007 | Ban ............ G06Q 10/10 705/2 |
| 7,628,730 B1 | 12/2009 | Watterson et al. |
| 7,749,056 B2 | 7/2010 | Ando et al. |
| 7,931,563 B2 | 4/2011 | Shaw et al. |
| 7,934,983 B1 | 5/2011 | Eisner |
| 7,946,959 B2 | 5/2011 | Shum et al. |
| 8,188,868 B2 | 5/2012 | Case, Jr. |
| 8,287,383 B1 | 10/2012 | Etter et al. |
| 8,287,436 B2 | 10/2012 | Shum et al. |
| 8,292,743 B1 | 10/2012 | Etter et al. |
| 8,313,416 B2 | 11/2012 | Ellis et al. |
| 8,444,491 B2 | 5/2013 | Bethke et al. |
| 8,491,395 B2 | 7/2013 | Auterio et al. |
| 8,496,532 B1 | 7/2013 | Bethke et al. |
| 8,506,409 B2 | 8/2013 | Bethke et al. |
| 8,556,778 B1 | 10/2013 | Dugan |
| 8,608,570 B1 | 12/2013 | Mahajan et al. |
| 8,784,273 B2 | 7/2014 | Dugan |
| 2002/0002600 A1* | 1/2002 | Yamada ............ G06F 17/3087 709/219 |
| 2002/0022516 A1 | 2/2002 | Forden |
| 2002/0035593 A1* | 3/2002 | Salim ............ G06F 17/3089 709/202 |
| 2002/0080035 A1 | 6/2002 | Youdenko |
| 2002/0082065 A1 | 6/2002 | Fogel et al. |
| 2002/0082077 A1 | 6/2002 | Johnson et al. |
| 2002/0090985 A1 | 7/2002 | Tochner et al. |
| 2002/0151992 A1 | 10/2002 | Hoffberg et al. |
| 2002/0160883 A1 | 10/2002 | Dugan |
| 2002/0163495 A1 | 11/2002 | Doynov |
| 2003/0208113 A1* | 11/2003 | Mault ............ A61B 5/14532 600/316 |
| 2004/0023761 A1 | 2/2004 | Emery |
| 2004/0053690 A1 | 3/2004 | Fogel et al. |
| 2005/0068169 A1 | 3/2005 | Copley et al. |
| 2005/0101845 A1 | 5/2005 | Nihtila |
| 2005/0177051 A1 | 8/2005 | Almen |
| 2005/0275541 A1 | 12/2005 | Sengupta et al. |
| 2006/0025282 A1 | 2/2006 | Redmann |
| 2006/0031102 A1 | 2/2006 | Teller et al. |
| 2006/0089543 A1* | 4/2006 | Kim ............ A61B 5/00 600/300 |
| 2006/0122474 A1 | 6/2006 | Teller et al. |
| 2006/0224051 A1 | 10/2006 | Teller et al. |
| 2006/0264730 A1 | 11/2006 | Stivoric et al. |
| 2006/0281543 A1 | 12/2006 | Sutton et al. |
| 2007/0004482 A1 | 1/2007 | Ando et al. |
| 2007/0038038 A1 | 2/2007 | Stivoric et al. |
| 2007/0053513 A1 | 3/2007 | Hoffberg |
| 2007/0111858 A1 | 5/2007 | Dugan |
| 2007/0167204 A1 | 7/2007 | Lyle et al. |
| 2007/0173705 A1* | 7/2007 | Teller ............ A61B 5/02055 600/300 |
| 2007/0197274 A1 | 8/2007 | Dugan |
| 2007/0208233 A1 | 9/2007 | Kovacs |
| 2007/0260482 A1 | 11/2007 | Nurmela et al. |
| 2008/0027337 A1 | 1/2008 | Dugan et al. |

(56) References Cited

U.S. PATENT DOCUMENTS

| | | |
|---|---|---|
| 2008/0094226 A1 | 4/2008 | O'Shea et al. |
| 2008/0129518 A1 | 6/2008 | Carlton-Foss |
| 2008/0146892 A1 | 6/2008 | LeBoeuf et al. |
| 2008/0167861 A1 | 7/2008 | Inoue et al. |
| 2008/0191864 A1 | 8/2008 | Wolfson |
| 2008/0218310 A1 | 9/2008 | Alten et al. |
| 2008/0281633 A1 | 11/2008 | Burdea et al. |
| 2008/0318679 A1 | 12/2008 | Tran et al. |
| 2009/0005140 A1 | 1/2009 | Rose et al. |
| 2009/0048493 A1 | 2/2009 | James et al. |
| 2009/0099785 A1 | 4/2009 | Yamamoto |
| 2009/0121894 A1 | 5/2009 | Wilson et al. |
| 2009/0270743 A1 | 10/2009 | Dugan et al. |
| 2009/0282002 A1* | 11/2009 | Reeder .................. G06Q 30/02 |
| 2010/0033303 A1 | 2/2010 | Dugan et al. |
| 2010/0160041 A1 | 6/2010 | Grant et al. |
| 2010/0240458 A1 | 9/2010 | Gaiba et al. |
| 2010/0287011 A1 | 11/2010 | Muchkaev |
| 2011/0065504 A1 | 3/2011 | Dugan et al. |
| 2011/0082008 A1 | 4/2011 | Cheung et al. |
| 2011/0190055 A1 | 8/2011 | Leyvand et al. |
| 2011/0260830 A1 | 10/2011 | Weising |
| 2011/0275483 A1 | 11/2011 | Dugan et al. |
| 2012/0115116 A1 | 5/2012 | Kronik |
| 2012/0252580 A1 | 10/2012 | Dugan |
| 2012/0253487 A1 | 10/2012 | Dugan |
| 2012/0253489 A1 | 10/2012 | Dugan |
| 2012/0306643 A1 | 12/2012 | Dugan |
| 2013/0006736 A1 | 1/2013 | Bethke et al. |
| 2013/0252731 A1 | 9/2013 | Dugan et al. |
| 2014/0011640 A1 | 1/2014 | Dugan |
| 2015/0066174 A1 | 3/2015 | Dugan |

FOREIGN PATENT DOCUMENTS

| | | |
|---|---|---|
| EP | 1 292 218 B1 | 4/2006 |
| EP | 1 702 560 A1 | 9/2006 |
| EP | 1 743 571 A2 | 1/2007 |
| JP | 59-170173 | 9/1984 |
| JP | 08103568 | 4/1996 |
| KR | 960007799 B1 * | 6/1996 |
| WO | WO 96/05766 A1 | 2/1996 |
| WO | WO 01/96986 A2 | 12/2001 |
| WO | WO 02/00111 A1 | 1/2002 |
| WO | WO 02/078538 A2 | 10/2002 |
| WO | WO 03/015005 A2 | 2/2003 |
| WO | WO 2004/019172 A2 | 3/2004 |
| WO | WO 2004/032715 A2 | 4/2004 |
| WO | WO 2004/034221 A2 | 4/2004 |
| WO | WO 2005/016124 A2 | 2/2005 |
| WO | WO 2005/027720 A2 | 3/2005 |
| WO | WO 2005/029242 A2 | 3/2005 |
| WO | WO 2005/092177 A1 | 10/2005 |

OTHER PUBLICATIONS

"Bluetooth." Wikipedia: The Free Encyclopedia. Aug. 10, 2009 <http://en.wikipedia.org/wiki/Bluetooth>.

Ichinoseki-sekine et al., "Improving the Accuracy of Pedometer Used by the Elderly with the FFT Algorithm," Medicine & Science in Sports & Exercise 2006,1674-1681.

Mann, W. et al., "Smart Phones for the Elders: Boosting the Intelligence of Smart Homes," Am. Assoc. for Artificial Intell., (AAAI), Jul. 2002.

Office Action of U.S. Appl. No. 13/456,190 dated Nov. 6, 2012.

May 6, 2013 Reply to Nov. 6, 2012 Office Action of U.S. Appl. No. 13/456,196.

Final Office Action of U.S. Appl. No. 13/456,196 dated Aug. 29, 2013.

Response to Final Office Action submitted with RCE of U.S. Appl. No. 13/456,196, filed Dec. 30, 2013.

Non-Final Office Action of U.S. Appl. No. 13/456,196 dated Dec. 5, 2014.

Non-Final Office Action of U.S. Appl. No. 14/536,599 dated May 11, 2015.

Notice of Abandonment of U.S. Appl. No. 13/456,196 dated Jun. 15, 2015.

Nov. 11, 2015 Reply to May 11, 2015 Non-Final Office Action of U.S. Appl. No. 14/536,599.

Final Office Action of U.S. Appl. No. 14/536,599 dated Feb. 24, 2016.

Interview Summary of U.S. Appl. No. 14/536,599 dated Apr. 14, 2016.

Notice of Appeal and Interview Summary of U.S. Appl. No. 14/536,599, filed Jun. 24, 2016.

Amendment Submitted with RCE of U.S. Appl. No. 14/536,599, filed Oct. 24, 2016.

Non-Final Office Action of U.S. Appl. No. 14/536,599 dated Nov. 21, 2016.

Feb. 21, 2017 Reply to Nov. 21, 2016 Non-Final Office Action of U.S. Appl. No. 14/536,599 dated Nov. 21, 2016.

Notice of Allowance of U.S. Appl. No. 14/536,599 dated Mar. 6, 2017.

Applicant-Initiated Interview Summary of U.S. Appl. No. 14/536,599 dated Oct. 28, 2016.

* cited by examiner

SYSTEMS AND METHODS FOR FITNESS AND VIDEO GAMES

This application is a continuation of and claims priority to U.S. patent application Ser. No. 14/536,599 filed Nov. 8, 2014, and titled "SYSTEMS AND METHODS FOR FITNESS AND VIDEO GAMES" which is a continuation of and claims priority to U.S. patent application Ser. No. 13/456,196 filed Apr. 25, 2012, and titled "SYSTEMS AND METHODS FOR FITNESS AND VIDEO GAMES", which claims priority to U.S. Provisional Patent Application No. 61/478,913, filed Apr. 25, 2011 and titled "SYSTEMS AND METHODS FOR FITNESS AND VIDEO GAMES" and which is a continuation-in-part of and claims priority to U.S. patent application Ser. No. 13/440,987, filed Apr. 5, 2012, and titled "SYSTEMS AND METHODS FOR FITNESS AND VIDEO GAMES", which claims priority to U.S. Provisional Patent Application No. 61/472,191, filed Apr. 5, 2011 and titled "SYSTEMS AND METHODS FOR FITNESS AND VIDEO GAMES" and which is a continuation-in-part and claims priority to U.S. patent application Ser. No. 13/433,285, filed Mar. 28, 2012 and titled "SYSTEMS AND METHODS FOR FITNESS AND VIDEO GAMES", which claims priority to U.S. Provisional Patent Application No. 61/468,444, filed Mar. 28, 2011 and titled "SYSTEMS AND METHODS FOR FITNESS AND VIDEO GAMES" and U.S. Provisional Patent Application No. 61/472,191, filed Apr. 5, 2011 and titled "SYSTEMS AND METHODS FOR FITNESS AND VIDEO GAMES".

Each of the above applications is hereby incorporated by reference herein in its entirety for all purposes.

FIELD OF THE INVENTION

The present application relates to fitness, and more particularly to systems and methods for fitness and video games.

BACKGROUND

A fitness craze has swept the United States and many other countries. From fat-free potato chips to treadmills, people around the world have become obsessed with weight loss and healthy living. Accordingly, record numbers of new fitness products/exercise equipment have emerged to meet this obsession (including stair climbers, treadmills, recumbent bicycles, ski machines, and the like).

Many pieces of exercise equipment, when used regularly, are very useful for weight loss, for improving cardiovascular stamina, and for strengthening various muscles. However, most exercise equipment suffers from a major drawback: the equipment is boring to use because of its inability to successfully encourage a user (e.g., an exerciser) to continue exercising. As a result, most purchasers of exercise equipment stop using the equipment shortly after purchasing it.

Numerous applications for mobile phones, tablet computers or the like are available for tracking fitness and exercise. Examples include applications that track food consumed, provide work out routines or the like. Such applications continue to grow in popularity.

However, a need exists for mobile applications and systems that motivate an exerciser to continue exercising, exercise harder and have fun.

SUMMARY

In some aspects, a system is provided that includes (1) a plurality of mobile devices; and (2) an application on each mobile device, the application adapted to (a) allow exercisers to form an exercise group; (b) track position or change in position of each exerciser in the exerciser group; and (c) display an avatar having a position that is controlled by a position or change in position of one or more member of the exercise group.

In some aspects, a method for exercising using a mobile device is provided that includes providing an application on a first mobile device. The application adapted to (1) display an avatar on the first mobile device; (2) monitor exercise performed by a user of the first mobile device to obtain monitored exercise information; (3) communicate monitored exercise information from the first mobile device to one or more other mobile devices employed by one or more other users; (4) receive monitored exercise information from one or more other mobile devices employed by one or more other users; (5) display an avatar on the first mobile device; and (6) adjust a position of the avatar on the first mobile device based on monitored exercise information of the first user and monitored exercise information from one or more other mobile devices.

In some aspects, an application for a mobile device is provided that includes program code adapted to allow the mobile device to (1) display a video game have one or more avatars controllable by location information of a user of the mobile device and location information of at least one user of another mobile device; (2) share location information for the mobile device with at least one other mobile device; and (3) obtain location information of at least one other mobile device.

In some aspects, a system is provided that includes a plurality of mobile devices and an application on at least a first mobile device. The application is adapted to track position information regarding the first mobile device, communicate the position information to a web server, receive position information from the web server regarding other mobile devices within a predetermined distance of the first mobile device, and use the position information regarding the other mobile devices to affect one or more characteristics of a video game executed on the first mobile device.

In some aspects, a method is provided that includes (1) executing a video game on a mobile device; (2) receiving position information regarding one or more additional mobile devices within a predetermined distance of the mobile device; and (3) using the position information regarding the one or more additional mobile devices to affect one or more characteristics of the video game executing on the mobile device.

In one or more aspects, an application for a mobile device includes program code adapted to allow the mobile device to (1) execute a video game on the mobile device; (2) receive position information regarding one or more additional mobile devices within a predetermined distance of the mobile device; and (3) use the position information regarding the one or more additional mobile devices to affect one or more characteristics of the video game executed on the mobile device.

In some aspects, an application is provided that is adapted to execute on at least a first mobile device. The application is adapted to (a) track information regarding a user of the mobile device; (b) create an avatar based on the tracked information; and (c) employ the avatar to provide preemptive warnings to assist in avoidance of unwanted behavior by the user.

Numerous other aspects are provided, as are various methods, apparatus and computer program products for carrying out these and other aspects of the invention. Each computer program product may be carried by a medium readable by a computer (e.g., a carrier wave signal, a floppy disc, a hard drive, a random access memory, etc.).

Other features and aspects of the present invention will become more fully apparent from the following detailed description, the appended claims, and the accompanying drawings.

DETAILED DESCRIPTION

Embodiments of the present invention provide systems and methods that motivate an exerciser to continue exercising, exercise harder and have fun during exercise. For example, in some embodiments, systems and methods are provided that allow an exerciser to employ a mobile phone, tablet or other similar portable computing device to join a group of exercisers in an exercising program.

Figure 1:
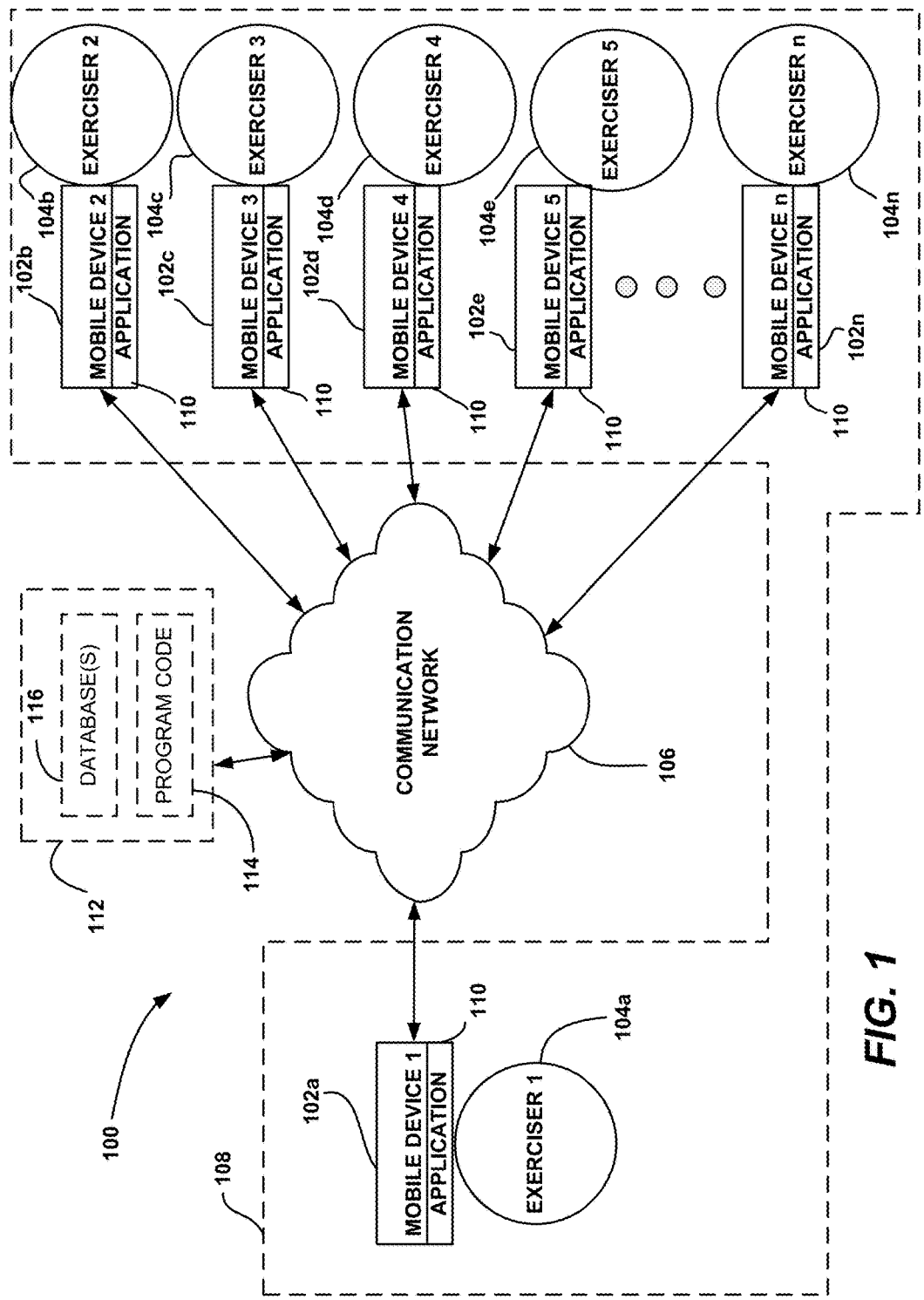
FIG. 1 illustrates a system for employing a mobile device to motivate an exerciser to exercise via communication with one or more other exercisers through one or more other mobile devices over a communication network in accordance with the present invention.

FIG. 1 illustrates a system 100 for employing a mobile device 102a to motivate an exerciser 104a to exercise via communication with one or more other exercisers 104b-n through one or more other mobile devices 102b-n over a communication network 106. The exercisers 104a-n may form an exercise group 108. Mobile devices 102a-n may include mobile (e.g., cellular) phones, other personal digital assistants (PDAs), tablet computers or the like which run an application 110 provided in accordance with the present invention and described further below. Exercisers 104a-n may be runners, cyclers, walkers or any other suitable exercisers. Communication network 106 may be the internet, one or more mobile telephone networks such as a 3G or 4G network, an intranet, a WiFi network or the like.

In one or more embodiments of the invention, each mobile device 102a-n may execute an application 110 that may:

(1) Employ GPS features of the mobile device to track position or change in position of the exerciser using the mobile device;

(2) Determine change in position information of the exerciser;

(3) Prompt the exerciser when and/or for how long the exerciser should change position;

(4) Determine speed information of the exerciser;

(5) Display a representation of the position, change in position, and/or speed of one or more exercisers on one or more of the mobile devices 102a-n;

(6) Communicate messages to one or more exercisers from one or more other exercisers;

(7) Monitor and/or communicate other biometric information of an exerciser such as heart rate, step rate, pulse, distance traveled, speed, etc.;

(8) Communicate position, change in position, heart rate, step rate, pulse, distance traveled, and/or other biometric information to one or more other exercisers, a third party such as family, friends, a doctor, an insurance company, a social network, etc.;

(9) Allow each exerciser to select an exercise group in which to participate; and/or

(10) Display information about the success of one or more exercisers and/or of the group at achieving a goal (e.g., time exercised, distance traveled, speed achieved, heart rate achieved, etc.).

In one particular embodiment, the application 110 may display information about and/or facilitate execution of a race in which each of the exercisers 104a-n may participate. For example, the race may be a relay race, a race between two destinations such as between two cities, across the island of Manhattan, across a state or the like, a race around the world, etc. Exerciser 104a (Exerciser 1) may be directed by mobile device 102a, such as by a visual and/or audio prompt, to exercise by walking, running, cycling or otherwise changing position for a predetermined time period and/or predetermined distance. In some embodiments, the application 110 may track the position of the exerciser 104a (exerciser 1) using a GPS feature of the mobile device 102a and communicate the position information to the exerciser 104a (exerciser 1) and/or to one or more of the mobile devices 102b-n of the exercisers 104b-n (and/or another third party if desired such as a family member, friends, retailers and/or restaurants near the exerciser, a social network site such as Facebook, Google+ or Twitter, etc). Each mobile device 102a-n may display a representation of the exerciser 104a's position (and/or change in position) as the exerciser 104a changes position. Other biometric information may be monitored, communicated and/or displayed such as heart rate, step rate, pulse rate, distance traveled, speed, etc.

Once the exerciser 104a (exerciser 1) completes his/her exercise such as by walking, running, cycling or otherwise changing position for the predetermined time period and/or predetermined distance, the second exerciser 104b (exerciser 2) may be begin exercising by walking, running, cycling or otherwise changing position for a predetermined time period and/or predetermined distance. In some embodiments, the application 110 may track the position of the exerciser 104b (exerciser 2) using a GPS feature of the mobile device 102b and communicate the position information to the exerciser 104b (exerciser 2) and/or to one or more of the mobile devices 102a, 102c-n of the exercisers 104a, 104c-n (exercisers 1, and 3-n). Each mobile device 102a-n may display a representation of the exerciser 104b's position (and/or change in position) as the exerciser 104b changes position. Other biometric information also may be monitored, communicated and/or displayed such as heart rate, step rate, pulse rate, etc. (In some embodiments, the periods in which exercisers exercise may overlap.)

The above process may repeat until each exerciser 104a-n has completed an exercise routine. For instance, each exerciser 104a-n may walk, run, cycle or otherwise change position one, two, three, etc., times during the race. Each exerciser 104a-n may exercise the same number or a different number of times during the race. While the above has been described with regard to exercisers changing position, it will be understood that other forms of exercise may be employed in which the exerciser does not change position significantly. For example, an exerciser may run or march in place, perform jumping jacks, etc., all of which may be detected by changes in acceleration measured by accelerometers within a mobile device such as a mobile phone, tablet computer, etc. Alternatively or additionally, heart rate, pulse, acceleration or other biometric monitors may monitor and/or provide biometric information to a mobile device and track exercise.

Figure 2A:
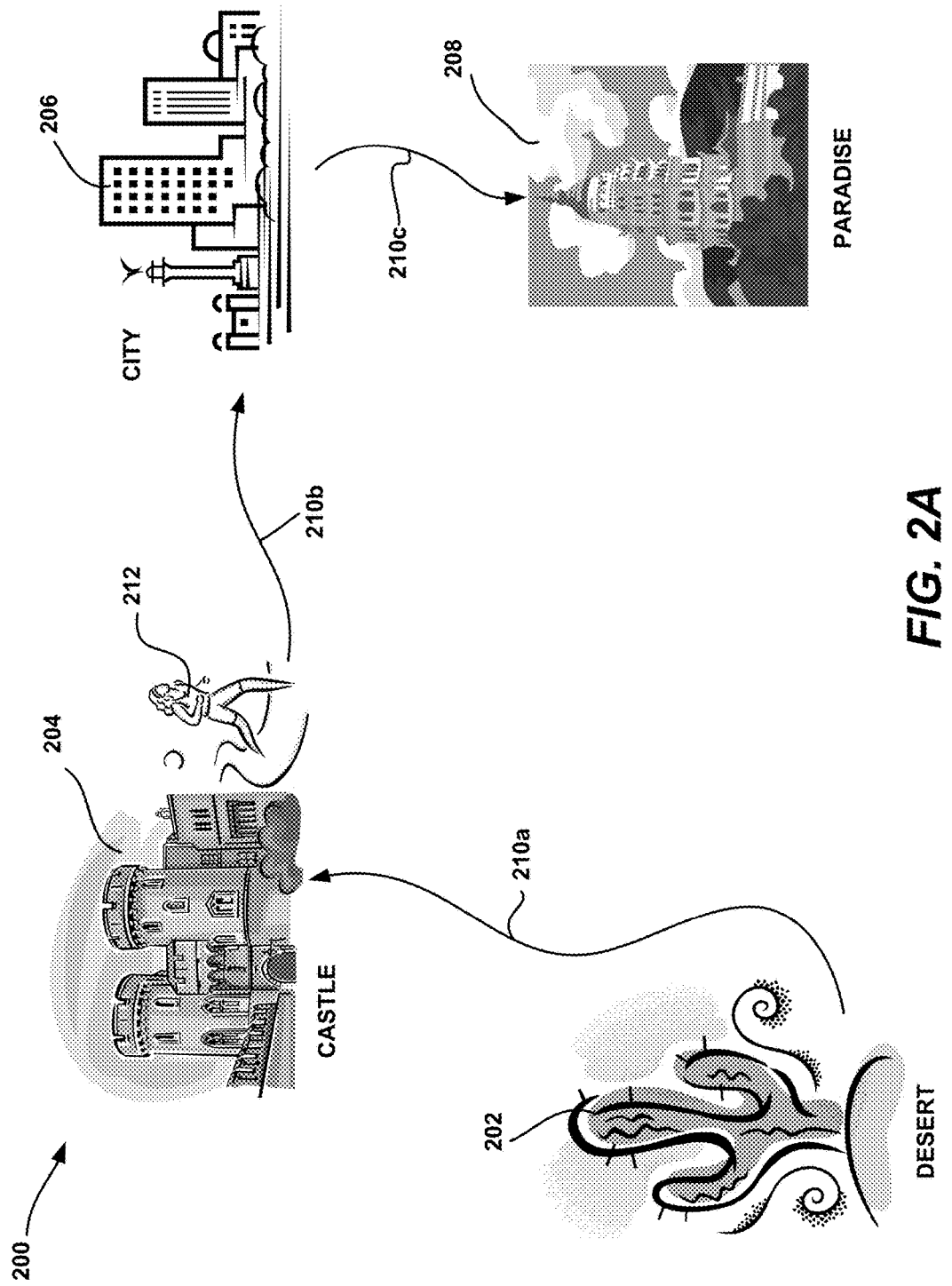
FIG. 2A-C are schematic diagrams of a first exemplary races in which a group may participate and which may be displayed on a mobile device in accordance with the present invention.
Figure 2B:
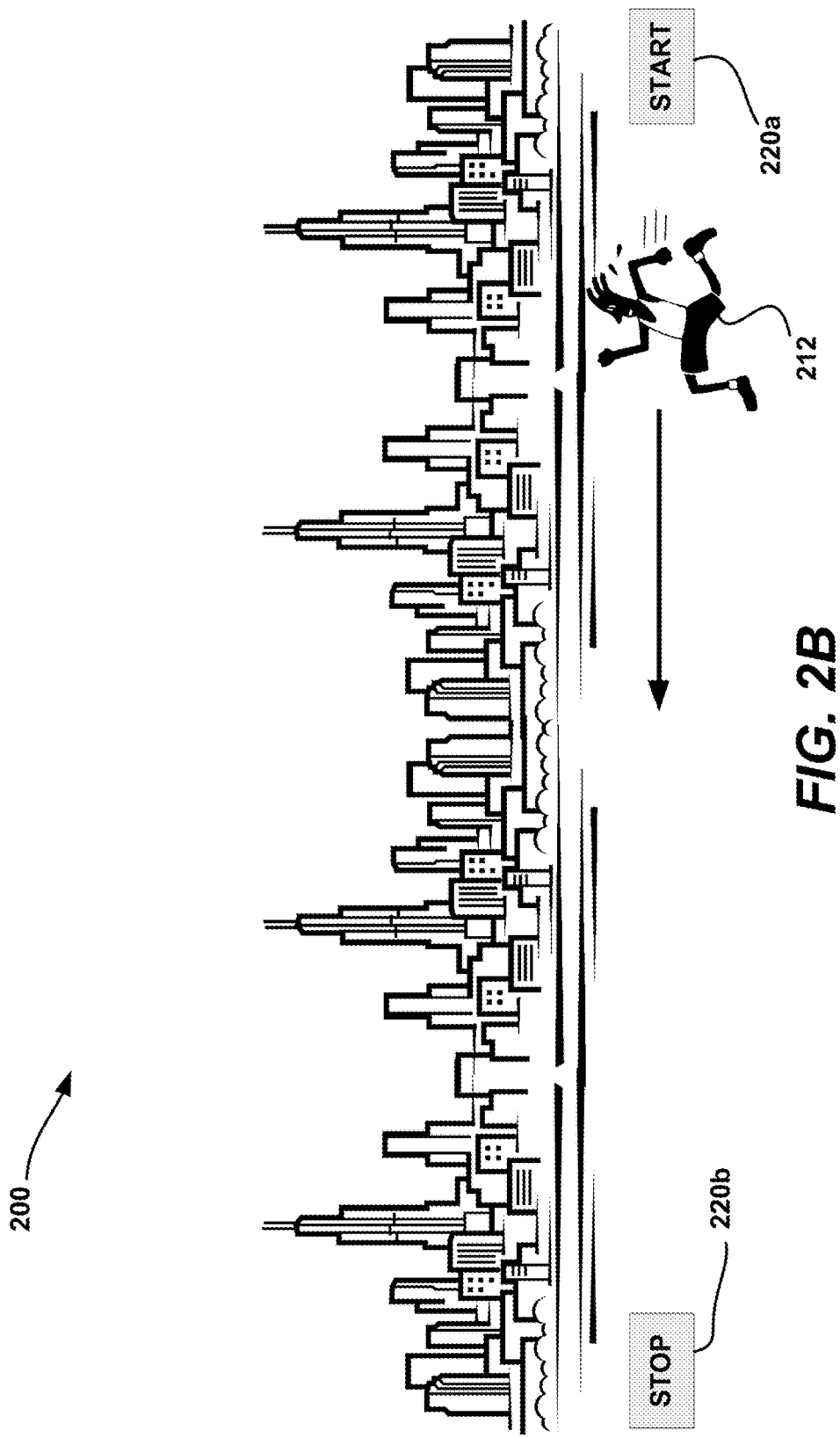

FIG. 2A is a schematic diagram of an exemplary race 200 in which the group 108 may participate and which may be displayed on each mobile device 102a-n using application 110. With reference to FIG. 2A, the race 200 includes four destinations including a desert 202, a castle 204, a city 206 and paradise 208 that are connected by paths 210a-c, respectively. An avatar 212 is shown traversing path 210b between castle 204 and city 206. Fewer, more and/or different destinations may be employed.

In operation, race 200 may be displayed on each mobile device 102a-n via application 110 running on each mobile device 102a-n. In general, each mobile device 102a-n need not be running application 110 simultaneously and exercisers 104a-n may launch application 110 at any time on a respective mobile device 102a-n (or any other suitable device) to check the status of avatar 212 within the race 200. In some embodiments, the program code for managing and/or administering race 200 (or any video game as described below) may reside on a Web server or other server 112 (FIG. 1) in communication with the mobile devices 102a-n and/or may be managed and/or administered by a social networking site such as Facebook, Google+ or Twitter. For example, web server 112 may include program code 114 and/or one or more databases 116 for managing and/or administering the race 200, storing information regarding exercisers 104a-n and/or their exercise activities, allowing new members to join the group 108, filtering potential new group members, etc. Likewise, race status and/or statistics may be displayed and/or viewed on such social networking sites or another web site.

With reference to FIGS. 1 and 2A, the position of avatar 212 is controlled by the exercise (e.g., such as change in position, heart rate, steps taken, other biometric parameters, etc.) of exercisers 104a-n. For example, exerciser 104a (exerciser 1) may be directed by mobile device 102a, such as by a visual and/or audio prompt, to exercise by walking, running, cycling or otherwise changing position for a predetermined time period and/or predetermined distance. In some embodiments, the application 110 may track the position of the exerciser 104a (exerciser 1) using a GPS feature of the mobile device 102a and display a change in position of the avatar 212 in response to a change in position of exerciser 104a. In this manner the avatar 212 may travel along paths 210a-210c between the various destinations 202-208. Each mobile device 102a-n may display the avatar 212 changing position as the exerciser 104a changes position. Each exerciser 104a-n may be assigned a portion or "leg" (portion) of the race 200 to complete by moving a predetermined distance or for a predetermined time period, or otherwise exercising. In some embodiments, the exercisers 104a-n may assist one another by offering encouragement, taking over the leg of the race 200 from another exerciser or the like. The avatar 212 may likewise change position based on biometric data measured for an exerciser such as heart rate, steps taken, pulse, etc.

Figure 2C:
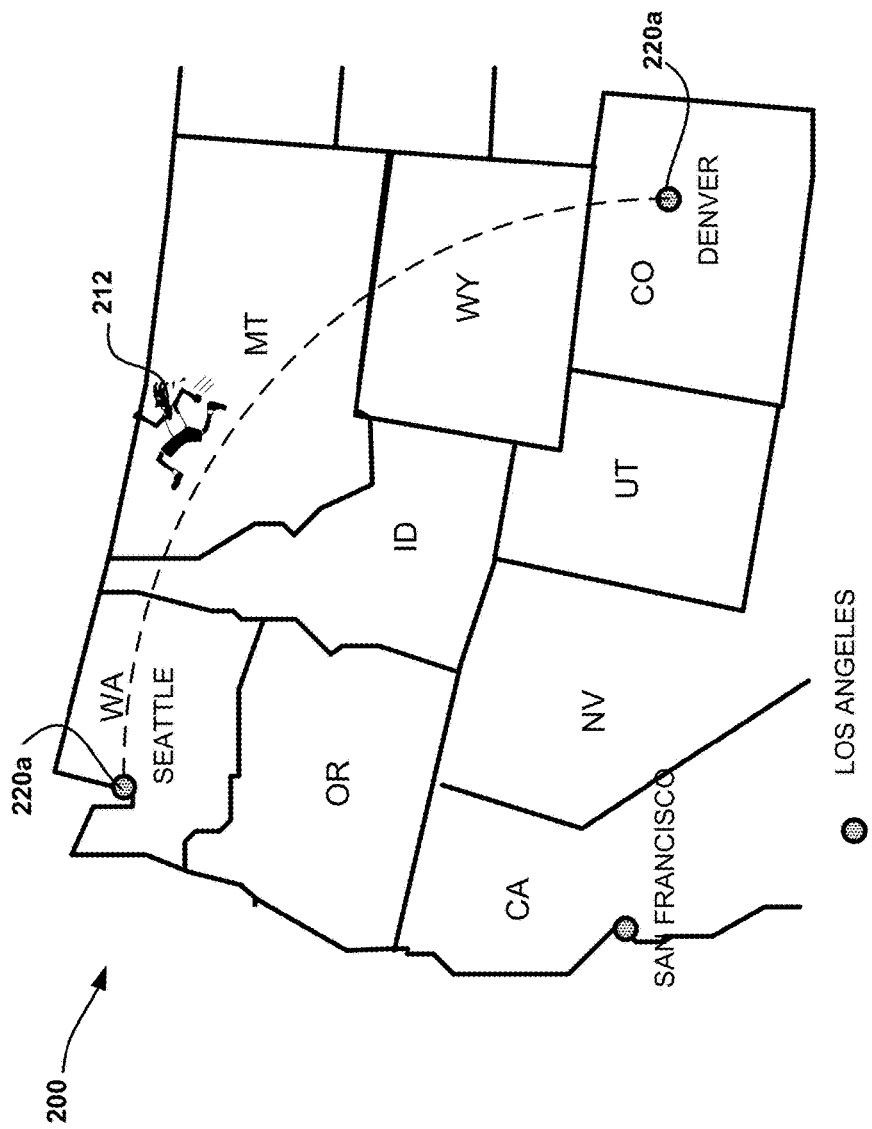

In one exemplary embodiment, the race 200 may be between two locations 220a and 220b, such as across Manhattan, Boston, San Francisco or the like and the avatar 212 may be shown progressing between the two locations 220a, 220b within the city in response to exercise performed by members of the exercise group 108. The "goal" of the race 200 may be to run across Manhattan or another city (e.g., by having the avatar 212 travel between the first and second locations 220a and 220b). Each exerciser 104a-n is motivated to do his/her part to help the group 108 and will experience how much the group can achieve by working together. This is even more pronounced in an embodiments such as shown in FIG. 2C in which avatar 212 travels between cities, such as between Manhattan and Boston, or Denver and Seattle as shown in FIG. 2C, or between any other remote locations (e.g., New York and China). In such embodiments, the avatar 212 is able to travel much farther through activities of the group 108 than would be possible through the activities of an individual. In some embodiments, the race 200 may take days, weeks, months or longer to complete and/or the distance traveled by avatar 212 may be the actual distance traveled by the members of the group 108 during exercise.

Figure 3:
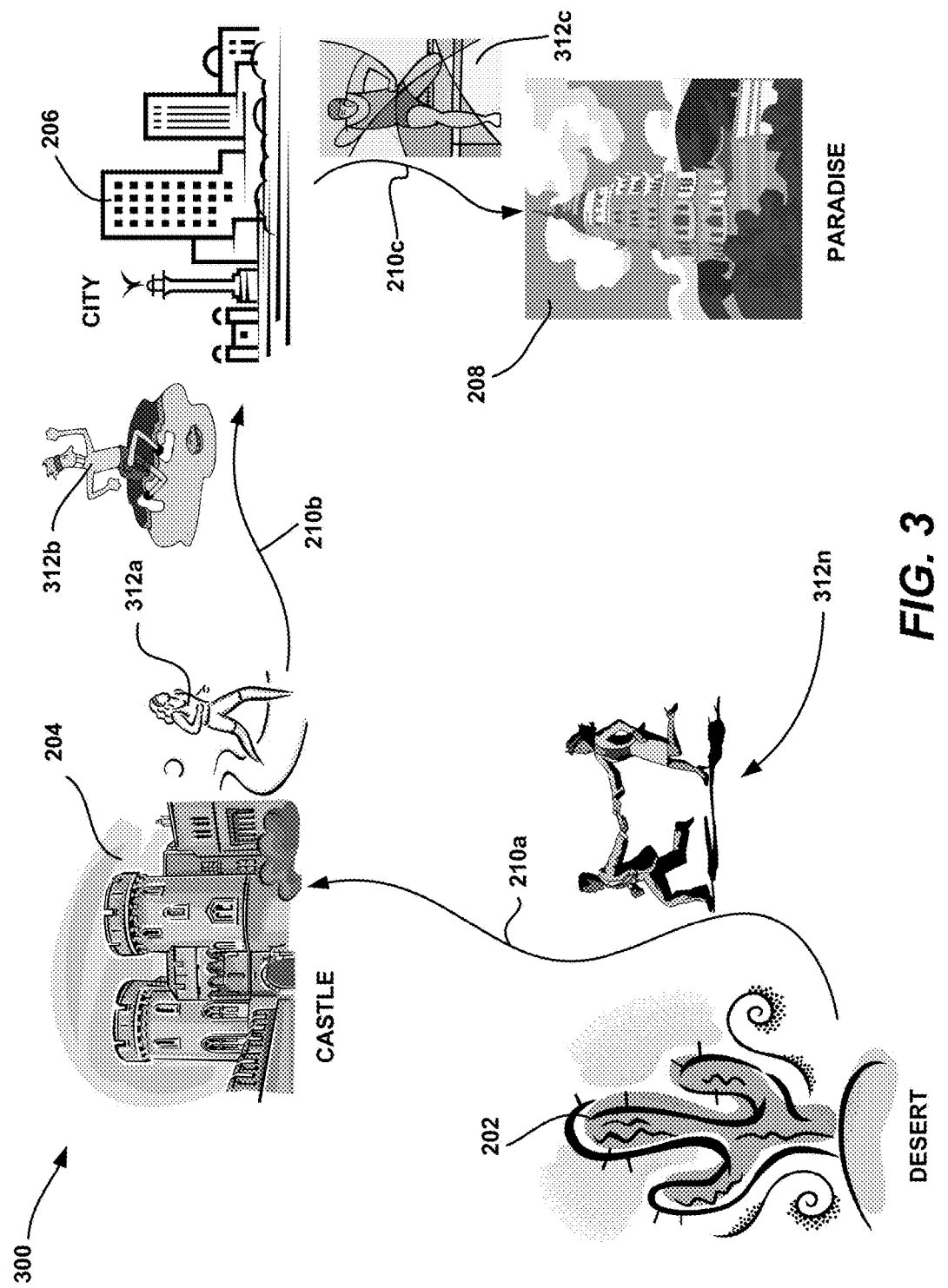
FIG. 3 is a schematic diagram of a second exemplary race in which a group may participate and which may be displayed on a mobile device in accordance with the present invention.

FIG. 3 is a schematic diagram of a race 300 in which multiple exercise groups 108 may compete with one another within the race 300. The race 300 is similar to the race 200, but includes a separate avatar 312a-n for each exercise group 108. In such embodiments, the mobile device of each exerciser in each group may be employed to display the race 300 and (multiple) avatar positions as the exercisers compete. Any number of exerciser groups may compete. In some embodiments, "handoffs" between exercisers within a group may be displayed as shown by avatar 312n which indicates that the current exerciser of an exercise group is ending his/her leg of the race and another member of the exercise group is beginning his/her leg of the race.

Exercisers within a group may not wish to share actual GPS coordinates with other members of their exercise group. Accordingly, in some embodiments, the application 110 may only communicate information representative of position or change in position of an exerciser to other mobile devices. For instance, when exerciser 104a begins his/her leg of a race, the application 110 on the mobile device 102a may treat the exerciser 104a as being at position x=0. Subsequent positions of the exerciser 104a may be adjusted accordingly so as to mask actual GPS coordinates of exerciser 104a. As mentioned, other biometric data such as heart rate, pulse rate, step rate, other parameters mentioned in Table 1 below, or the like may be monitored and employed to affect position, speed or the like of avatars 212 and/or 312a-n.

As stated, in some embodiments, the program code for managing and/or administering a race (or any video game as described below) may reside on a Web server or other server 112 in communication with the mobile devices 102a-n and/or may be managed and/or administered by a social networking site such as Facebook, Google+ or Twitter. In addition to races (e.g., travel from one location to another), other competitive sports activities may include a "virtual" baseball, dodge ball, tennis, hockey, lacrosse, kickball, etc., in which accelerometers within a mobile device are used to detect a kick, jump, swing of a baseball bat (or arm/hand that mimics a swing of a baseball bat), swing of a tennis racquet, hockey stick or lacrosse stick, or the like. For example, with reference to FIG. 4, an exercise group 108 may participate in a virtual baseball game 400 in which each exerciser 104a-n in the group 108 is assigned a position with an avatar 412a-n that is displayed in that position on a virtual baseball field 414 displayed on each mobile device 102a-n. In some embodiments, a remote web server, such as web server 112 in FIG. 1, may be programmed to communicate with the mobile device of each exerciser 104a-n, host the virtual game, issue avatar position updates to each mobile device used by an exerciser 104a-n (e.g., based on biometric or other information received from each mobile device as described below).

Figure 4:
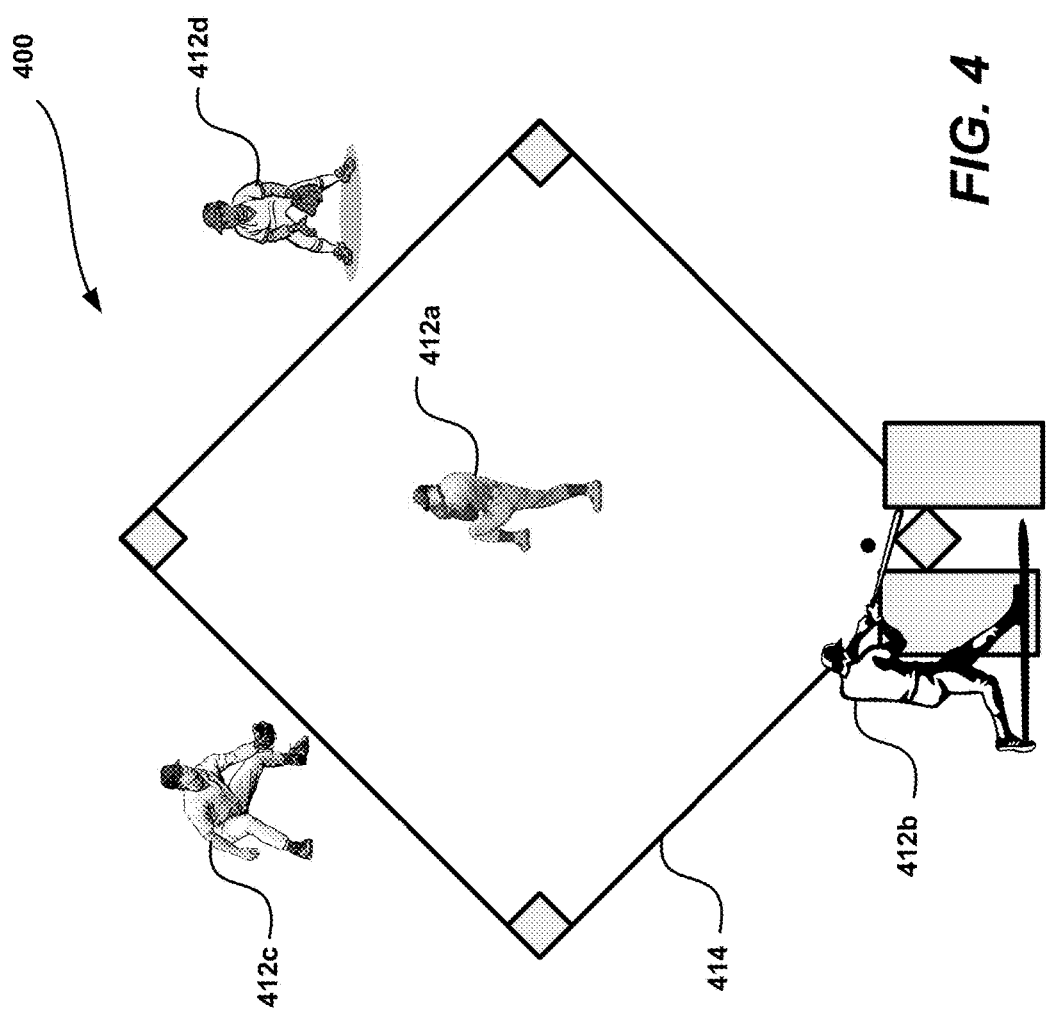
FIG. 4 is an exemplary baseball game in which a group may participate and which may be displayed on a mobile device in accordance with the present invention.

During a game, the position and/or behavior of each avatar 412a-d on a baseball field 414 may be controlled by the GPS location and/or other data measured by each mobile device 102a-n (and/or by biometric data collected by the mobile device 102a-n such as heart rate, speed, cadence, pulse, etc.). For example, exerciser 1 (represented by avatar 412a) may pitch a ball to exerciser 2 (represented by avatar 412b) by pretending to pitch a ball with his/her mobile device. For instance, exerciser 1 (represented by avatar 412a) may hold his/her mobile device in his/her pitching arm, and carry out a pitching motion while holding the mobile device. Accelerometers within the mobile device (or an accelerometer in communication with the mobile device) may measure forces generated during the pitch, for example, by measuring x, y and/or z axis acceleration. Each mobile device 102a-n may display an avatar representative of exerciser 1 pitching a ball and/or ball speed in the "virtual" game may be based on the real world pitch of exerciser 1 (e.g., as measured by accelerometers in the mobile device of exerciser 1, one or more external accelerometers in communication with the mobile device of exerciser 1 such as an accelerometer mounted in a write band, or the like). Exerciser 2 (represented by avatar 412b) may hit the ball pitched by exerciser 1 (represented by avatar 412a) by swinging his/her mobile device at the appropriate time based on the pitch of exerciser 1 (represented by avatar 412a) or by performing some predetermined exercise requirement (e.g., running for a predetermined time, distance and/or speed, maintaining a predetermined heart rate range for a predetermined time, or the like). Assuming exerciser 2 (represented by avatar 412b) actually hits the virtual ball (e.g., swings his/her mobile device at the correct time or performs a predetermined exercise requirement), each mobile device 102a-n may display a ball being hit by the avatar 412b of exerciser 2. Exerciser 3 (represented by avatar 412c), who may be playing infield or outfield, may catch the ball hit by exerciser 2 by running or performing some other predetermined exercise so as to cause his/her avatar 412c to run toward the virtual ball hit by the avatar 412b of exerciser 2. Exerciser 3 may "catch" the ball hit by exerciser 2 using his/her mobile device, for example. In general, all types of ball play may be similarly conducted using the accelerometers and/or GPS features of mobile devices 102a-n (or external biometric measurement devices that provide biometric information to the mobile devices). Other virtual games may be similarly played such as tennis, football, basketball, hockey, volleyball, or the like. While only four avatars are shown in FIG. 4 representing four exercisers, it will be understood that fewer or more exercisers and/or avatars may be employed.

Note that virtual game play may or may not be performed in real time. In some embodiments, the position or other characteristics of an avatar may be changed during or after exercise is performed.

In one or more embodiments, an exercise group, such as a group of friends, a group with members that share certain characteristics such as similar age, interests, historical exercise performance, education, or the like (which in some embodiments may be identified via a social networking site), may agree to play a virtual game while each group member works out. For instance, one group member may wish to work out at a local gym, while another may wish to work out in his/her home, etc. As described above, each gaming device such as a cellular telephone, tablet computer, etc., may include an application which displays a video game in which each group member may control one or more aspects of the video game. For instance, each group member's exercise may control the position, speed, movement or the like of a video game character. In this manner a group of friends may be motivated to work out together. Similarly, an exerciser may enter a "pick up" game with previously unknown exercisers. In a further example, such games may be used in a match-making embodiment (e.g., to introduce people with similar interests and/or geographic location that meet predetermined criteria such as age, education, marital status, or the like). For example, a first exerciser may be at a local health club and wish to meet another exerciser within the health club. He/she may send out a request for someone within the health club to participate and/or compete in a video game or virtual competition. In some embodiments, an application on a mobile device may be used to access a social networking cite to identify exercise partners. That is, application 110 may access a web site to identify exercisers at the health club. For instance, the health club may maintain a Facebook or similar page that may be used to identify exercisers currently at the health club that may wish to interact, such as train or compete, with other exercisers at the health club. The request may include filters such as required characteristics of the invited exerciser (e.g., female, single, age, employment status, etc.). Accordingly, an application with such functionality may be provided to execute on a mobile device or other gaming device of the exercisers. Specifically, in some embodiments, application 110 may include computer program code that allows an exerciser to indicate a desire to participate with local exercisers; identify the current location of the exerciser (e.g., using GPS features of the mobile device executing application 110 or by selection by the exerciser); and communicate position information to a web site. The web site may employ geographical information about the exerciser to identify other nearby exercisers that have indicated a desire to exercise with others. The web site may then introduce the exercisers (e.g., by specifying where the exercisers can meet or by introducing avatars of the exercisers on respective mobile devices). In some embodiments, the web site may host a virtual game/race as described above. Any suitable biometric information may be monitored during exercise such as position, speed, heart rate, cadence, etc.

Figure 5:
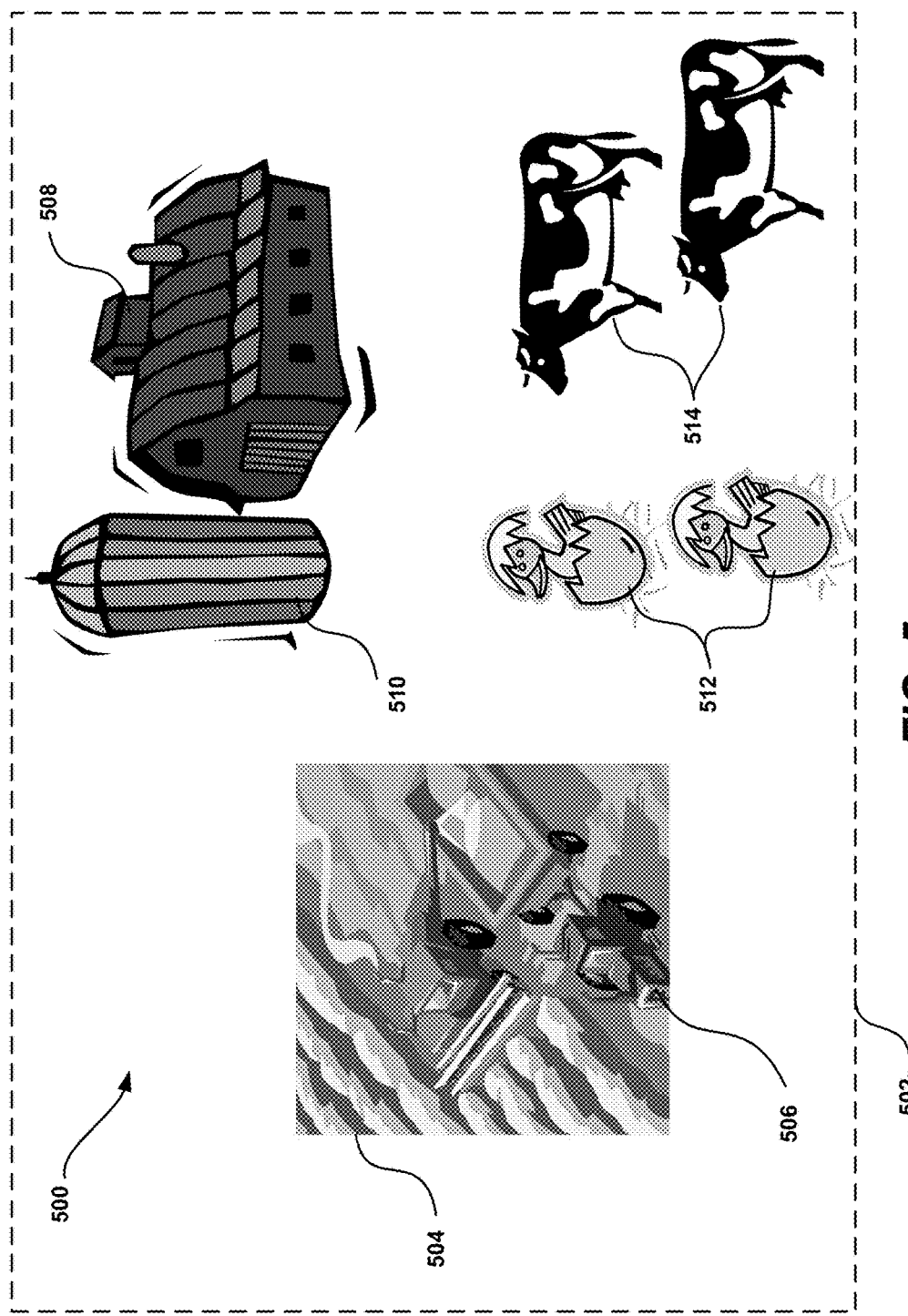
FIG. 5 is an exemplary social network game in which a group may participate and which may be displayed on a mobile device in accordance with the present invention.

FIG. 5 is a schematic diagram of an exemplary video game 500 for use by mobile devices 102a-n via a Web server or other server 112 in communication with the mobile devices 102a-n and/or may be managed and/or administered by a social networking site such as Facebook, Google+ or Twitter. In the embodiment of FIG. 5, a virtual farm 502 is provided that includes crops 504, a tractor 506, a barn 508, a silo 510, chickens 512, cows 514 and/or any other typical farm items (not shown). In some embodiments, the goal of such a video game 500 may be to grow more crops, buy more land, obtain more eggs, chickens, cows or milk, plow fields, harvest crops, or the like. In accordance with embodiments of the present invention, performance of such activities may be enhanced by exercise of one or more exercisers 104a-n. For instance, if exerciser 104a is playing the video game 500, exerciser 104a may be assigned (or establish) an exercise goal such as a number of miles to walk or run, a number of minutes to walk or run on a treadmill, a length of time to perform an aerobics routine, a number of jumping jacks to perform, etc. Completion of such goals may be monitored by a mobile device 102a-n as previously described (e.g., through use of accelerometers of the mobile device or external accelerometers, GPS-features, use of heart rate monitors, verification by a third party such as a friend or health club staff, etc.). In exchange for completion (or partial completion) of the exercise goal, an exerciser may be rewarded with more land, more or heartier crops, more cows or more milk production from cows, new farm animals or equipment, gas or diesel fuel for farm equipment, more grain in the silo 510, more tokens or virtual money for farm item purchases, or the like.

In some embodiments, an exercise group 108 may be assigned to a farm (e.g., a community farm). Exercisers 104a-n within the exercise group 108 may be assigned farm tasks that are enhanced by exercise as described above. Being a part of such a group may be provide additional motivation for each exerciser 104a-n to complete regular exercise (e.g., due to peer pressure).

In some embodiments, an application 110 for a mobile device is provided that includes program code adapted to allow the mobile device to display and interact with a virtual farm having one or more avatars controllable by location and/or other exercise information of a user of the mobile device. For example, the application 110 may track location and/or other exercise information such as heart rate, pulse, steps, etc., and reward the exerciser with enhanced game play within the virtual farm environment (e.g., more land, more or heartier crops, more cows or more milk production from cows, new farm animals or equipment, gas or diesel fuel for farm equipment, more grain in the silo, more tokens or virtual money for farm item purchases, or the like). In one or more embodiments, the application 110 may share location information with at least one other mobile device and/or obtain location information of at least one other mobile device. In some embodiments, the program code may be adapted to allow a user of the mobile device to join an exercise group and communicate with mobile devices of other members of the exercise group (e.g., within the virtual environment).

Other Embodiments

The exercisers 104a-n may wish to have a more interactive experience. Accordingly, in some embodiments, the race 200 and/or 300 may be part of a video game in which the avatar 212 and/or avatars 312a-n encounter monsters, snipers, assassins, wild animals, obstacles or other typical video game scenarios that the avatar(s) must navigate through and/or survive. In this regard, if exerciser 104a is currently exercising, his/her exercise level may directly affect video game play of either the exerciser 104a or of the other exercisers 104b-n. For instance, exercise of exerciser 104a may be employed to affect the speed, striking force, game level, etc., of the avatar 212. Exemplary video game character performance levels that may be affected by a measured exercise parameter are shown below in Table 1. Such parameters may be measured using suitable sensors such heart rate monitor chest straps, pedometers, accelerometers, or the like.

TABLE 1

| MONITORED EXERCISER PERFORMANCE LEVEL | VIDEO GAME CHARACTER PERFORMANCE LEVEL CONTROLLED |
|---|---|
| pedaling rate | speed, striking force |
| stepping rate | speed, striking force |
| rowing rate | speed, striking force |
| running rate | speed, striking force |
| pulse rate | speed, energy level, accuracy |
| striking force | striking force |
| swing velocity | swing velocity |
| distance traveled | game level |
| time exercised | game level |

In one example, exercise of exerciser 104a may be used to control speed, striking force or game level of a video game in which avatar 212 is a character. One or more of the other exercisers 104b-n in group 108 may control other parameters of the avatar 212 such as movement to the right, left, up, down, other movements such as jumping, kicking, firing a weapon, steering a car, etc. For instance, while exercising, the exerciser 104a may not be free to use his/her hands to manipulate the mobile device 102a in a manner that would cause the avatar 212 to turn right or left, kick, jump, fire a weapon, etc. Nonetheless, the exercise of the exerciser 104a may be used to affect the speed, striking force, game level, etc., of the avatar 212. One or more of the other exercisers 104b-n in group 108 who is/are not exercising may use his/her respective mobile device 102b-n to cause movement of the avatar 212 to the right or left, to kick, etc., or otherwise proceed through the video game (e.g., using accelerometers within the mobile device, tapping the screen of the mobile device, etc.) while the exerciser 104a is exercising.

Figure 6:
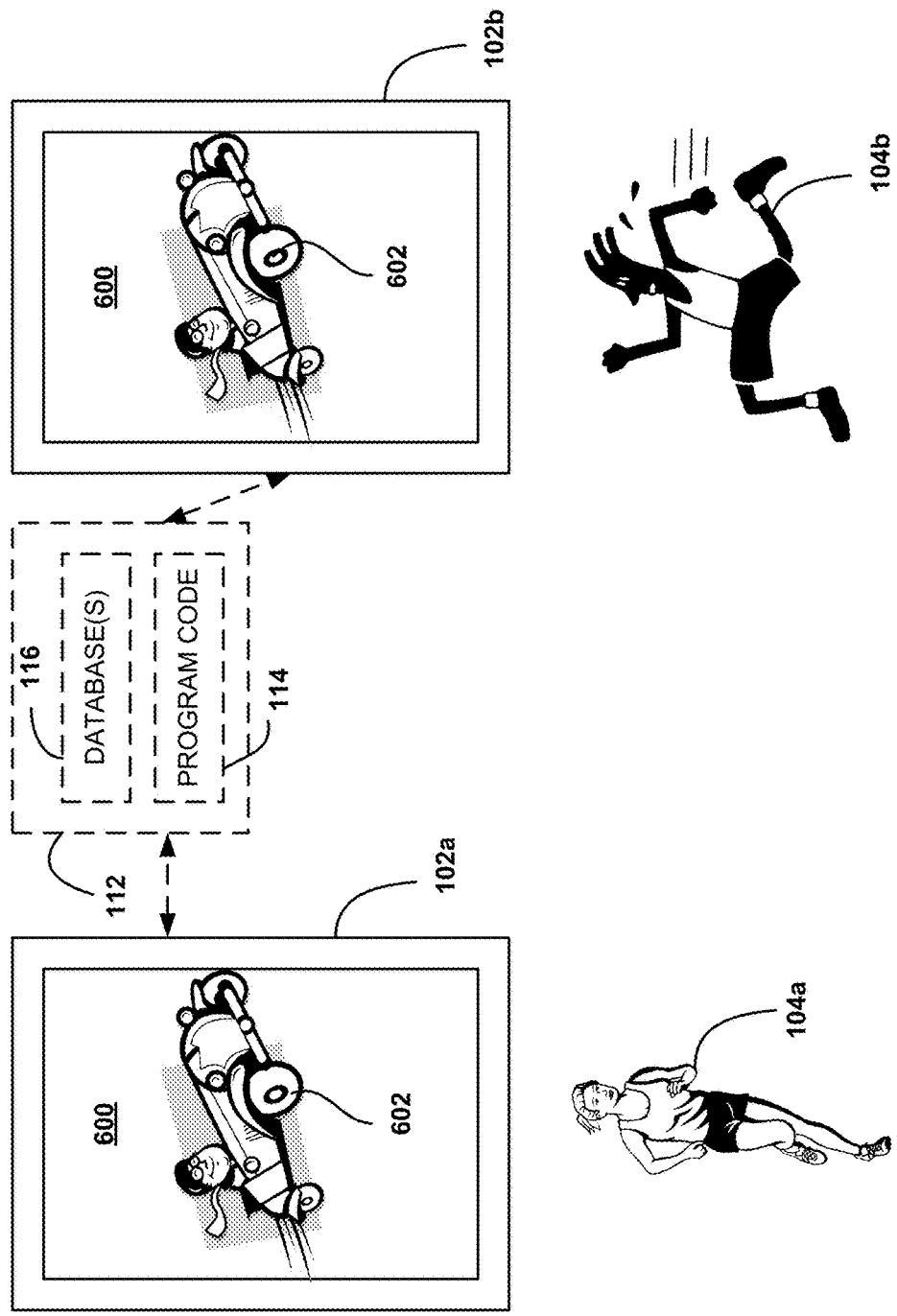
FIG. 6 is an exemplary car race in which a group may participate and which may be displayed on a mobile device in accordance with the present invention.

In some embodiments, primary control of the avatar 212 may pass back and forth between two or more members of an exercise group over and over during a work out routine (e.g., as the person exercising changes). For example, FIG. 6 is a schematic diagram of a video game 600 executing on mobile devices 102a and 102b of exercisers 104a and 104b, respectively. Other numbers of mobile devices and/or exercisers may be used.

Mobile devices 102a-b include an application for the video game 600. In the example shown, a race car 602 is shown. Any other video game type, character, setting or the like may be used (as described above, for example). Mobile devices 102a-b may communicate with each other directly, such as via WIFI, a cellular network, some other protocol, etc., or may communicate indirectly through a web server 112 or similar system. In the embodiment shown, control of the steering and/or braking of car 602 is controlled by the exerciser 102a or 102b who is not exercising, while control the speed of the car 602 is controlled by the exerciser 102a or 102b who is exercising. Who exercises when and/or for how long may be determined by the exercisers 102a, 102b, a third party such as other members of an exercise group, a trainer, a retailer that may offer rewards for completing an exercise program, or the like. For instance, in some embodiments, web server 112 may host a web interface in which the race 600, or information or statistics about the race 600, may be observed. Through such a web interface, an exerciser or other party may enter a desired exercise duration for the game 600, when and/or for how long each exerciser will exercise, etc. Such information may be communicated to the mobile devices 102a-n before and/or during game play, for example.

In one or more embodiments, a mobile device 102a may include an application 110 having computer program code adapted to (1) log into a web site; (2) indicate a desire to join an exercise group and/or select an exercise group to join; (3) specify duration and/or type of exercise desired; (4) specify who in a group will exercise when and/or for how long; (5) receive an indication from the web site when an exerciser should begin exercising; (6) receive updates from the web site regarding how an exerciser within the group is progressing; (7) display changes in the video game in response to exercise (e.g., change in position of an avatar in response to exercise performed by members of the group); (8) display changes in the video game in response to inputs from members of the group (e.g., direction, speed or other behavior of an avatar); and/or (9) allow users to control one or more aspects of the video game when not exercising (e.g., direction, speed, or other behavior of an avatar). In some embodiments, a web site hosting such a group may offer incentives, rewards or the like to group members for being in the group, achieving exercise objectives, etc., (e.g., coupons to restaurants, virtual tokens or rewards for on-line social games, etc.).

In other embodiments, the exerciser 104a may control movements of an avatar as well. In one particular embodiment, an application 110 may be adapted to process voice commands of the exerciser 104a to control movement or other behaviors of an avatar. Exemplary voice commands are shown in Table 2 below.

TABLE 2

| VOICE COMMAND OF EXERCISER | VIDEO GAME CHARACTER CHARACTERISTIC CONTROLLED |
| --- | --- |
| "L" or "Left" | turn left |
| "R" or "Right" | turn right |
| "J" or "Jump" | jump |
| "D" or "Duck" | duck or drop to the ground |
| "B" or "Back" | move back |
| "K" or "Kick" | kick |
| "F" or "Fly" | fly |

In other embodiments, another sound of exerciser 104a may be used to control the avatar, such as a "clacking" sound. For instance, the exerciser 104a may clack his/her tongue once to turn right, twice to turn left, thrice to jump, etc., similar to Morse code. In some embodiments, the exerciser 104a may select/record sounds that are to be interpreted by the application 110 to correspond to turning left or right, jumping, ducking, kicking with a left or right leg, flying, etc.

Additional Embodiments

Figure 7:
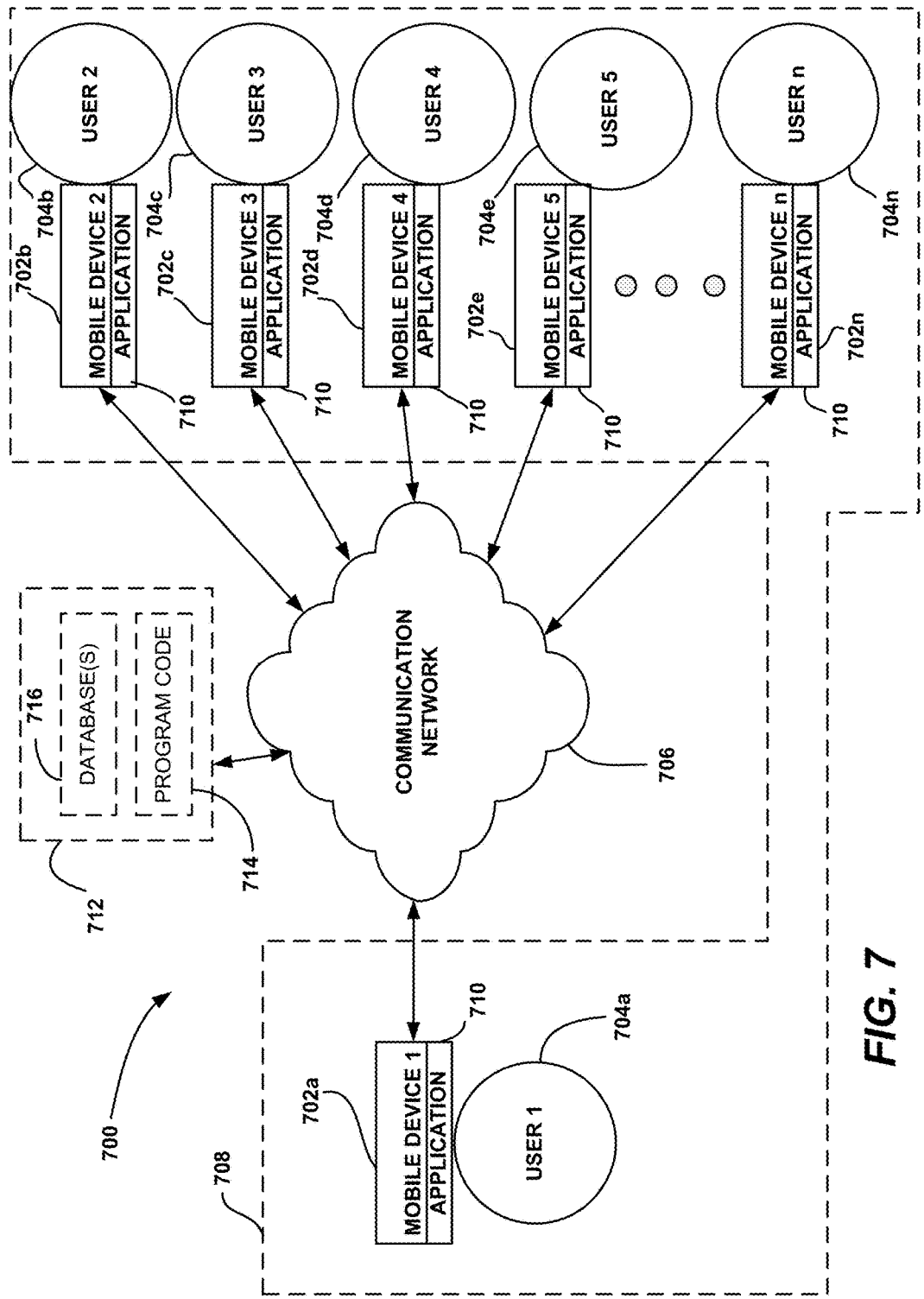
FIG. 7 is a schematic diagram of a system for employing proximity of other mobile device users to affect game play in accordance with the present invention.

In some embodiments, a gaming device such as a mobile telephone, tablet computer, or the like, may include a video game with characteristics that change based on the number of other gaming devices near the gaming device. For example, FIG. 7 is a schematic diagram of a system 700 for employing proximity of other mobile device users to affect game play. With reference to FIG. 7, a plurality of mobile devices 702a-n associated with users 704a-n are shown each running an application 710. Fewer or more mobile devices and/or users may be present. Application 710 is adapted to communicate over a communication network 706 to a web server 712 (having program code 714 and one or more databases 716).

In operation, application 710 may be executed on numerous mobile devices such as cellular telephones, tablet computers or the like. Each mobile device executing application 710 may communicate location information regarding its respective mobile device to web server 712 and web server 712 may collect, aggregate and/or otherwise assemble location information. In some embodiments, web server 712 analyzes the collected location information to determine a group 708 of mobile devices 702a-n that are within a predetermined distance of each other (e.g., same room, building, block, city, state, etc.). The distance may be selected by the web server 712, or in some embodiments, based on a user of a mobile device (e.g., mobile device 102a in this example). For instance, user 704a may wish to play a video game having characteristics that vary based on the number of people near the user 704a at any given time. User 704a may specify what distance away from the user 704a a person must be to affect game play (e.g., 10, 20 or 30 feet, 100 yards, same city block, 1 mile, same city, etc.). Web server 712 then may communicate with the application 710 executing on mobile device 702a to communication how many people (e.g., mobile device users) are near user 704a. Application 710 may include a video game, or interact with another video game on mobile device 702a, so that the number of people specified by web server 712 affects game play on mobile device 702a. Alternatively or in additional, web server 712 may provide position information, or relative position information to mobile device 702a, for mobile users near user 704a, and application 710 may use this information to affect game play. For instance, a number, density, location, or the like of background characters in a video game may be based on the information provided by web server 712 (e.g., an opposing team's army size, the number of monsters in a game, the density of a forest in the game, or any other relevant video game parameter). In this manner, a dynamically changing video game is provided that is affected by real world activities. Note that application 710 need not be identical on each mobile device 702a-n (e.g., some applications 710 may be communicating information to web server 712 for other purposes).

In general, the application 710 may monitor whether mobile devices are within a predetermined geographic area of one another, such as by using GPS location information from each mobile device. Characteristics of a video game running on one or more of the mobile devices may depend on or otherwise be affected by the number or proximity of other mobile devices (e.g., video game characteristics such as the number or position of video game characters within the video game, the landscape or background characteristics of the video game, etc.). In some embodiments, biometric information collected by each mobile device such as heart rate, speed, etc., similarly may be used to affect the video game by affecting the speed, strength, position, etc., of characters within the video game). Further, in some embodiments, certain game levels, movements, etc., may only be possible within the video game if a large enough (or small enough) number of mobile devices are present within a predetermined location (e.g., if enough people are at a restaurant, concert, or other venue). For instance, a restaurant, concert hall or other venue may host a gaming event and provide incentive within the venue or with the video game based on a number of attendees (e.g., free food, higher gaming level, etc.).

In some embodiments, the video game may communicate with a social networking site such as Facebook, Google+ or Twitter, and such social networking sites may identify or notify friends or affiliated groups of the presence of friends or members within a particular geographic area (e.g., using GPS features of mobile devices). Such friends or affiliated groups may be prompted to participate in video games or to otherwise interact.

In one or more embodiments, video game characteristics of a video game may be affected by location information of the mobile device executing the video game. For instance, a user may only enter a certain game level if he/she is physically located at a particular location such as a restaurant, a mall, a computer store, a city, a monument, or the like. The user's position may be determined, for example, using GPS features of the mobile device (e.g., mobile device 702a may do this directly, or mobile device 702a may communicate position information to web server 712, and web server 712 may provide access to the game level or other benefit based on the position information).

In yet other embodiments, location information from mobile devices may be collected and/or aggregated to track position, travel habits, etc., of a group of people such as lawyers, doctors, gamers, etc., that are members of a social network. In fact, a virtual world or map may be generated by tracking the position of one or mobile devices during any given time period. In some embodiments, such information may be used to affect video game characteristics such as game environment, number of video game characters, or the like. For instance, web server 712 may collect position information for members of a legal group on a networking web site and provide this information for use in a video game (e.g., as described above).

In some embodiments of the invention, a system is provided that includes a plurality of mobile devices and an application on at least a first mobile device. The application is adapted to track position information regarding the first mobile device, communicate the position information to a web server, receive position information from the web server regarding other mobile devices within a predetermined distance of the first mobile device, and use the position information regarding the other mobile devices to affect one or more characteristics of a video game executed on the first mobile device.

In one or more embodiments, a user of the first mobile device may select how position information affects the video game (e.g., what characteristics of the game are affected by the number of people near the user, such as a number of enemies in the video game, landscape, game level, etc.), and/or the predetermined distance. Alternatively, the web server may select one or more of how position information affects the video game and the predetermined distance. The position information may include a number of other mobile devices within the predetermined distance, a density of mobile devices, or any other relevant position information. In some embodiments, the web server may provide incentives if a predetermined number of mobile devices are within the predetermined distance, such as coupons or discounts to restaurants or other retail establishments.

The foregoing description discloses only exemplary embodiments of the invention; modifications of the above disclosed apparatus and method which fall within the scope of the invention will be readily apparent to those of ordinary skill in the art. For instance, any number of performance levels of an exerciser may be monitored and used to control any number of performance levels of a video game character. Further, old video games may be modified for use with the present invention, or new video games may be developed.

In some embodiments, exercisers may join exercise groups via a social networking site such as Facebook, Google+ or Twitter. Such social networking sites may collect information on the exercisers and make recommendations for exercise groups based on age, weight, type of exercise, geographic location or the like.

In some embodiments, exercisers training for a marathon or other exercise goal may be identified by a social networking site (e.g., based on hobbies, interests, or other identifying data posted by the exerciser on the social networking site). One or more exercisers, or the social networking site itself, may invite like exercisers to join a training group. In some embodiments, retail businesses such as clothing stores, restaurants, cellular telephone providers, or the like, may offer members of the group discounts such as reduced rate clothing, discounted meals, reduced cell phone rates or free minutes (e.g., for calls between group members) or the like.

In some aspects, a method for exercising using a mobile device is provided that includes providing an application on a first mobile device. The application adapted to (1) display an avatar on the first mobile device; (2) monitor exercise performed by a user of the first mobile device to obtain monitored exercise information; (3) communicate monitored exercise information from the first mobile device to one or more other mobile devices employed by one or more other users; (4) receive monitored exercise information from one or more other mobile devices employed by one or more other users; (5) display an avatar on the first mobile device; and (6) adjust a position of the avatar on the first mobile device based on monitored exercise information of the first user and monitored exercise information from one or more other mobile devices. The monitored exercise information may exchanged between mobile devices via a remote web server, such via a social network web site running on the remote web server.

In some aspects, an application for a mobile device is provided that includes program code adapted to allow the mobile device to (1) display a video game have one or more avatars controllable by location information of a user of the mobile device and location information of at least one user of another mobile device; (2) share location information for the mobile device with at least one other mobile device; and (3) obtain location information of at least one other mobile device. In some embodiments, the program code may be adapted to allow a user of the mobile device to join an exercise group; and communicate location information for the mobile device with mobile devices of other members of the exercise group. In some embodiments, the program code may be adapted to communicate with mobile devices of other members of the exercise group through a social network web site. In additional embodiments, the program code may be adapted to switch control of motion of the avatar on the mobile device between the user of the mobile device and a user of another mobile device.

In some embodiments, one or more of the methods or processes described above may be implemented, at least in part, in computer program code and/or may form a computer program product. Each computer program product may be carried by a medium readable by a computer (e.g., a carrier wave signal, a floppy disc, a hard drive, a random access memory, etc.). In general, information about a user (e.g., an exerciser) may be provided to the server 112 or another computer by any mechanism (e.g., via mail, via e-mail, via telephone, via cellular telephone, via facsimile, etc.). For example, information may be received via one or more HTTP transmissions or via some other communications protocol.

In some embodiments, a mobile device, such as a smart phone or tablet computer, may be in communication with one or more sensors so as to receive biometric information. The mobile device may communicate the biometric information to one or more third parties to obtain discounts (e.g., an insurance company to receive discounted insurance rates, a restaurant to receive reduced meal prices, a weight loss clinic to receive discounted membership fees, or the like).

In some embodiments, a mobile device such as a smart phone or tablet computer may collect fitness and exercise information about a person using one or more biometric sensors as previously described. In addition (or alternatively), the mobile device may collect other information about the person such as:

(1) travel habits such as where, when, how often, traveled etc., (e.g., via a GPS feature of the mobile device, tower triangulation, via Internet searches conducted on the mobile device, via interactions with travel websites on the mobile device, by providing surveys/questions on the mobile device, by collecting information from social networking cites using the mobile device, etc.);

(2) sleep habits such as amount of sleep, time of sleep, quality of sleep (e.g., based on monitored sleep cycles, by providing surveys/questions on the mobile device, by collecting information from social networking cites using the mobile device etc.);

(3) relationship information such as demographic information, type of friends preferred, number of friends, status of relationships, etc. (e.g., by providing surveys/questions on the mobile device, by collecting information from social networking cites using the mobile device, etc.);

(4) spending habits such as amount, frequency or type of spending, how spending is performed (e.g., cash, check, credit card), time of day spending occurs, what influences spending such as a commercial, time of day, weather, mood, etc. (e.g., by providing surveys/questions on the mobile device, by collecting information from social networking cites using the mobile device, by monitoring on-line bill payments made via the mobile device, via payments made using the mobile device, etc.);

(5) call information such as typical parties called, talk time, time of day calls are made, etc. (e.g., via call information logged by the mobile device);

(6) work habits such as times worked, type of work, how work affects mood, etc. (e.g., by providing surveys/questions on the mobile device, by collecting information from social networking cites using the mobile device, etc.);

(7) music and/or movie/television preferences (e.g., by monitoring characteristics of playlists of music on the mobile device such as type of music, artist, or the like, by monitoring videos viewed on the mobile device such as type of movie or television show, actors or actresses in the videos or the like, by providing surveys/questions on the mobile device, by collecting information from social networking cites using the mobile device, etc.);

(8) drinking habits such as how often, time of day, type of drink, mood, triggers for drinking, etc. (e.g., by providing surveys/questions on the mobile device, by collecting information from social networking cites using the mobile device, etc.);

(9) smoking habits such as how often, time of day, type of cigarette, duration of smoking, mood, triggers for smoking, etc. (e.g., by providing surveys/questions on the mobile device, by collecting information from social networking cites using the mobile device, etc.);

(10) emotional state information such as mood at any given time of the day, how weather, seasons, family, friends, co-workers, strangers, travel, vacation, being alone, etc., affects emotional state, etc. (e.g., by providing surveys/questions on the mobile device, by collecting information from social networking cites using the mobile device, by detecting stress levels using biometric information measured with the mobile device such as heart rate, perspiration, etc.);

(11) health information such as current health, historical health information such as when illnesses have occurred in the past, how weather, seasons, family, friends, co-workers, strangers, travel, vacation, being alone, etc., affects health, etc. (e.g., by providing surveys/questions on the mobile device, by collecting information from social networking cites using the mobile device, by accessing electronically available patient records of a user of the mobile device such as through medical provider website/portals, etc.); for instance, a mobile application on mobile device may be provided that allows a user to indicate that he/she has a cold, a flue, allergies, etc.; the mobile application may correlate this information with time of day, day of year, season, weather, or the like;

(12) online activity such as purchases, spending, searches performed, stock purchases, etc. (e.g., via transactions conducted on the mobile device or by communicating transactions from other computing devices of the user to the mobile device, by providing surveys/questions on the mobile device, by collecting information from social networking cites using the mobile device, etc.); and

(13) any other suitable information.

In some embodiments, much of the above information may be obtained directly from a mobile device via a suitable mobile application executing on the mobile device. However, some information such as mood, emotional state, etc., may be obtained by prompting a user of the mobile device to respond, such as with a mobile application that collects information from the user. Upon collection, the above data may be aggregated and used to form a "model" of the mobile device user that may be used to predict and/or guide future behavior, health, mood, etc. Further, an "intelligent avatar" may be created based on the data model. The intelligent avatar may react in a manner similar to that of the mobile device user if exposed to similar stimuli (e.g., in a virtual environment). Accordingly, in some embodiments, avatar behavior and/or appearance may be based on real world characteristics of the avatar's owner (e.g., the user of the mobile device) such as exercise, location, sleep, travel, other lifestyle parameters, weather or the like.

In some embodiments, an avatar may travel with its owner. For example, an avatar (e.g., characteristics of the avatar) may be stored, such as a wrist band or USB drive, or on a mobile device such as a tablet or smart phone.

In some embodiments, an avatar may take on personal preferences and habits, and assist in decisions or provide warnings. For example, a mobile application executing on a user's mobile device may track any of the above described information and based on a model of the user's behavior, predict that the user is about to engage in destructive behavior such as overeating, drinking, smoking, or the like (e.g., by recognizing one or more triggers for the destructive behavior). The user's avatar may provide a warning of such impending action and try to mitigate the triggers, contact family or support group members, etc. In some embodiments, a wrist band may include a stimulation device that may vibrate, shock or otherwise alert and/or obtain the attention of a person who wears the wrist band in response to a signal from the mobile device (e.g., sent wirelessly). User behavior, habits, etc., may be modeled on personal data and data collected by a smart phone or tablet computer to develop an "avatar conscience" that may be used to assist the user in making decisions.

In some embodiments, social networks may be built by avatars. For example, like avatars may be identified and/or "interact" (compare data) based on physical proximity, existing social networks or groups, etc. Intelligent avatars may interact (compare data) to determine compatibility prior to a real word meeting of owners of the avatars. Users may comment on, rank or otherwise critique avatars as part of developing historical avatar characteristics.

Figure 8:
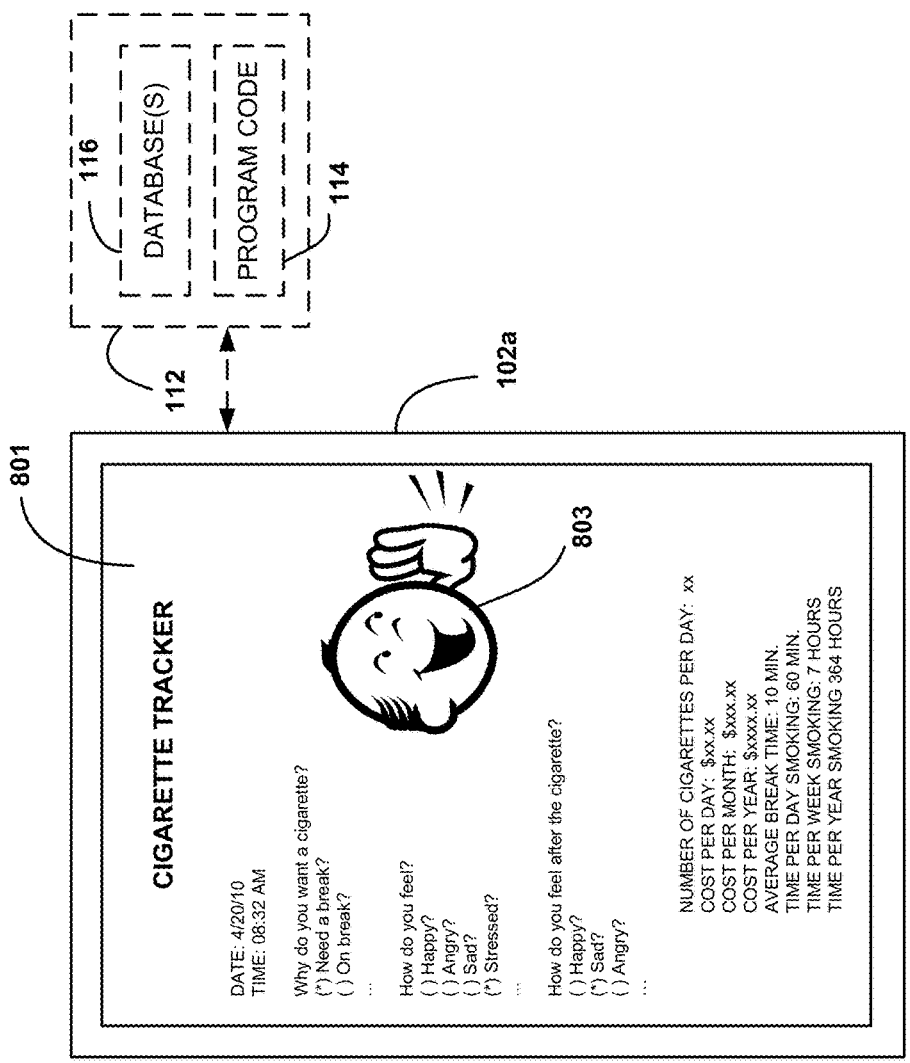
FIG. 8 is a schematic diagram of an application for tracking smoking habits executing on a mobile device of a user in accordance with the present invention.

FIG. 8 is a schematic diagram of an application 801 executing on mobile device 102a of a user (not shown). The application 801 includes computer program code for performing the various steps described below and/or one or more databases for storing information about the user. In some embodiments, all or a portion of the program code and/or database(s) may be located on a remote server 112 (as illustrated by program code 114 and database(s) 116 in FIG. 8).

Application 801 is adapted to track cigarette use of a user. For example, each time a user of the mobile device 102a wishes to have a cigarette, the user may execute application 801 on mobile device 102a (or application 801 may automatically execute based on predetermined settings such as certain times of day, certain day of the week, etc., selected by a user or a third party such as a doctor or family member, based on stress level of the user measured by biometric sensors such as heart rate monitors, pulse monitors, etc., or the like). In some embodiments, an avatar 803 may provide (advanced) warning to the user that he/she will likely smoke if behavior is not altered (e.g., acting as a "conscience" for the user as previously described).

Application 801 may prompt the user with a number of questions such as "Why do you want a cigarette?", "How do you feel?", "Are you hungry?", "Are you stressed?", "Are you having a bad day?" or the like. In some embodiments, in response to the above questions, the application 801 may attempt to substitute another activity for the user in place of smoking such as having a healthy snack, going for a walk, talking to a friend or family member (e.g., via a call list associate with the application 801), or the like. The application 801 may prompt the user to "clock-in and -out" during smoking so the application 801 may track the duration of the smoking break. In this manner, the application 801 may track smoking statistics such as number of cigarettes smoked per day, week, year, etc., cost of cigarettes per day, week, year, etc., amount of time spent smoking, etc. In some embodiments, such activities may be used to predict life expectancy for the user. Further in some embodiments, an avatar representative of the user (e.g., avatar 803) may be created having lifetime, health or other characteristics affected by the user's smoking habits (e.g., the avatar's lifeline or energy level may decrease with each cigarette smoked, the avatar's appearance may degrade with each cigarette smoked, etc.). Such clear communication of the cost, time and health implications of smoking may reduce the number of cigarettes smoked by the user. Likewise, times of the day during which a user is most likely to smoke may be identified and substitute activities may be automatically executed by the application 801 during such times to distract the user (e.g., video game play, infomercials, meditation programs, etc.). Cigarette consumption statistics may be provided to third parties such as doctors, family members, or the like.

Figure 9:
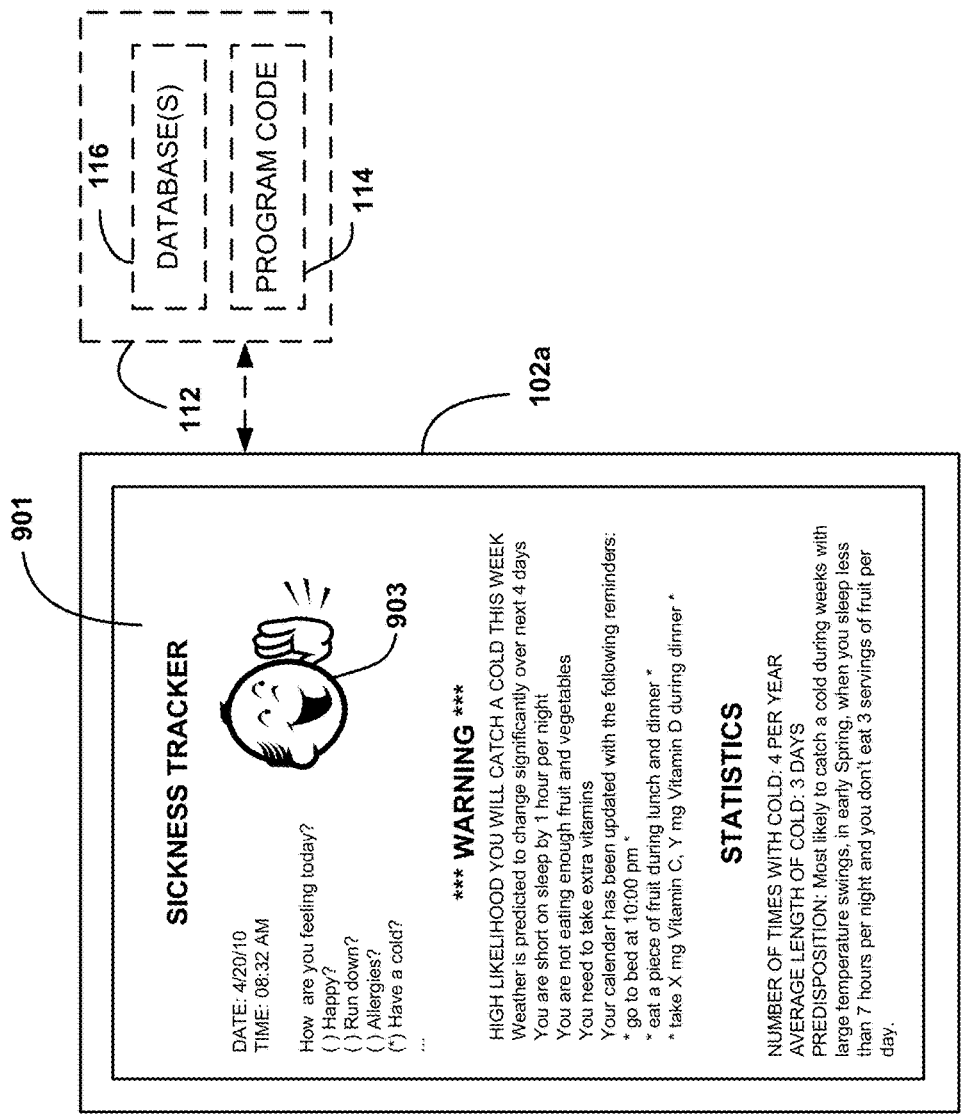
FIG. 9 is a schematic diagram of an application for tracking health executing on a mobile device of a user in accordance with the present invention.

FIG. 9 is a schematic diagram of an application 901 executing on mobile device 102a of a user (not shown). The application 901 includes computer program code for performing the various steps described below and/or one or more databases for storing information about the user. In some embodiments, all or a portion of the program code and/or database(s) may be located on a remote server 112 (as illustrated by program code 114 and database(s) 116 in FIG. 9).

Application 801 is adapted to track health of a user of the mobile device. For example, one or more times a day, the user may execute application 901 on mobile device 102a (or application 901 may automatically execute based on predetermined settings such as certain times of day, certain day of the week, etc., selected by a user or a third party such as a doctor or family member). Application 901 may prompt the user with a number of questions such as "How are you feeling today?" "How did you sleep last night?" "How many hours did you sleep last night?", "Do you have a cold?", "Are you suffering from allergies?", "Did you take your vitamins?", "What did you eat for breakfast, lunch or dinner?" or the like. The application 901 also may collect information about local weather, pollen count, the US economy or any other factors that may affect a person's well being (e.g., as some people catch colds more often during dramatic changes in temperature, some people experience extra stress when the stock market drops, some people suffer from allergies or asthma during high pollen counts, etc.). In some embodiments, in response to the above questions, the application 901 may attempt to encourage corrective activities for the user (and/or issue warnings) such as having a healthy snack, going for a walk, talking to a friend or family member (e.g., via a call list associate with the application 801), taking one or more vitamins, going to bed earlier (e.g., application 901 may automatically generate alarm reminders at the appropriate time (e.g., employing the user's calendar) telling the user to get ready for bed, take a vitamin, exercise, etc.) or the like. In some embodiments, such activities may be used to predict life expectancy for the user (or of an avatar representation of the user such as avatar 903). Further in some embodiments, an avatar representative of the user may be created having lifetime, health or other characteristics affected by the user's habits (e.g., the avatar's lifeline or energy level may increase or decrease with each user choice such as food eaten, vitamins taken, amount of sleep, etc.). (Avatar 903 also may provide warnings/advice of impending destructive behavior or otherwise provide suggestions based on past behavior of the user as previously described). In this manner, the application 901 may track activities/statistics such as number of days sick per year, average length of cold, cost of sickness or poor habits in terms of salary or productivity, when the user is predisposed to catch a cold (or flu), etc. Such clear communication of the cost, time and health implications of lifestyle choices may encourage positive behaviors/healthy choices. Statistics regarding user activities may be provided to third parties such as doctors, family members, or the like.

Figure 10:
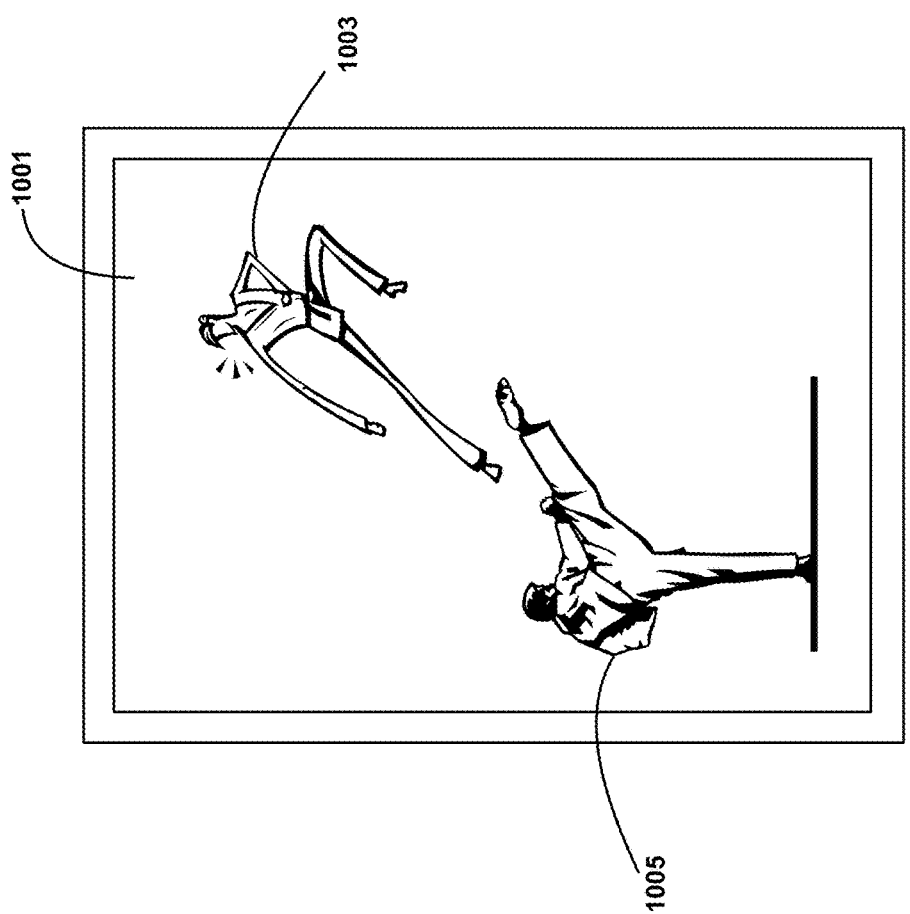
FIG. 10 is a schematic diagram of another exemplary video game executing on a mobile device in accordance with the present invention.

FIG. 10 is a schematic diagram of a video game 1001 executing on a mobile device 102a. In the example shown, a karate avatar 1003 is shown fighting another karate character 1005. Any other video game type, character, setting or the like may be used (as described above, for example). Karate avatar 1003 may have one or more characteristics based on data collected about the user of the mobile device 102a. As described above, information such as eating habits, sleeping habits, smoking habits, drinking habits, stress level, weather, market conditions, pollen count, spending habits, other information described above or other relevant information may be used to affect characteristics of the karate avatar 1003. For instance, if the user of the mobile device 102a is sick, his/her avatar may exhibit reduced performance such as by being slower, kicking lower, having a reduced lifetime, etc. In some embodiments, corrective or positive activities undertaken by the user of the mobile device 102a may improve performance of the avatar 1003. For instance, if the user of the mobile device 102a is prompted by the mobile device 102a to take a vitamin, get more rest, eat more fruit, etc., in response to the user performing the requested task, performance of avatar 1003 may improve (e.g., immediately, for a predetermined time such as until the next scheduled activity is requested by the mobile device 102a such as taking another vitamin or other medicine). In some embodiments, karate character 1005 may have one or more characteristics based on a data collected about another mobile device user.

Figure 11:
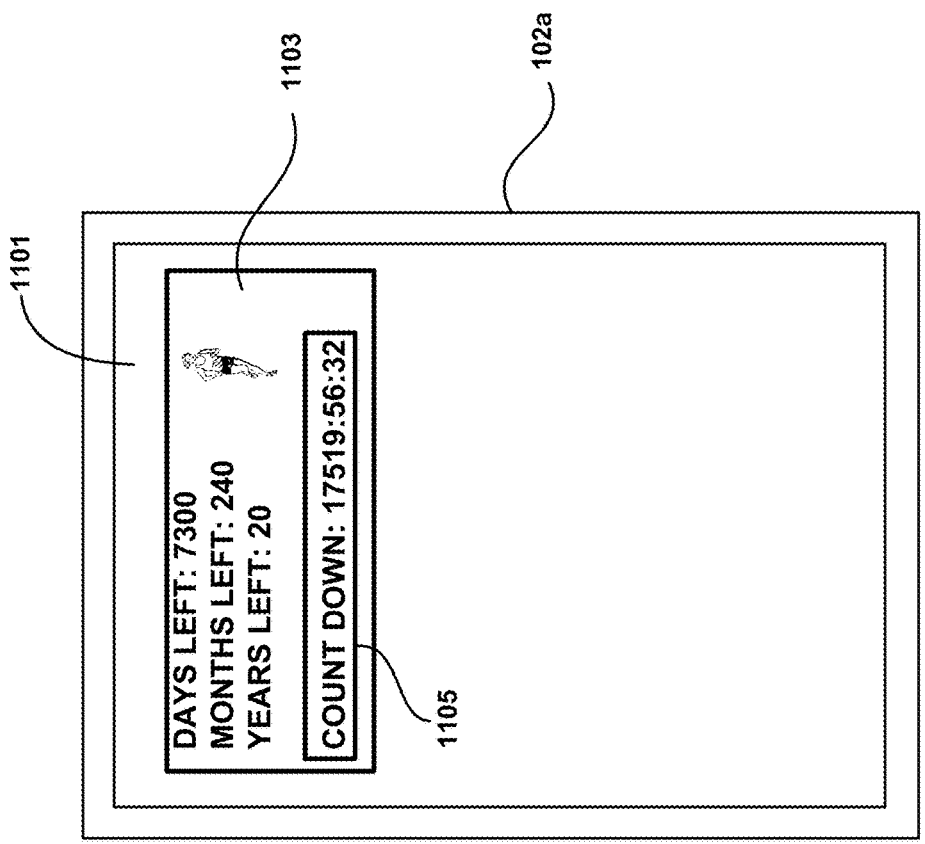
FIG. 11 illustrates an application that may display life expectancy information and/or a count down clock on a mobile device in accordance with the present invention.

In some embodiments, based on the above described data or any other data collected or otherwise obtained by a mobile device, a count down clock may be created for a user. For example, FIG. 11 illustrates an application 1101 that may display a window 1103 with life expectancy information and/or a count down clock 1105 on a mobile device 102a. The count down clock and/or life expectancy information may predict, based on actuarial data and/or any of the above described information, how long the user may expect to live. In some embodiments, the time/statistics may change based on monitored behavior, habits, actions, etc., of the user. For example, food intake, exercise, stress level, sleep, etc., may affect the life expectancy of the user (e.g., a user may see in real time or fairly contemporaneously how good or bad habits affect life expectancy). In some embodiments, the count down clock and/or life expectancy information may relate to the user of the mobile device 102a or to an avatar representative of the user of the mobile device 102a. Note that the life expectancy data may be (strongly) skewed based on behavioral data to provide motivation for improved behavior. For example, the application 1101 may increase life expectancy by several days if a user eats fruit on any given day as a motivational tool (e.g., and then readjust the life expectancy downward later). For maximum effect, the window 1103 and/or count down clock 1105 may remain on display during execution of other programs, or serve as a screen saver.

Computer program code may be developed to execute one or more of the methods described above, and such computer code may take the form of an application executable on a mobile device such as a smart phone, tablet computer or the like.

In some embodiments, an application may be provided on a mobile device 102a that measures activities/behaviors of a user as described above and provides the user with a daily, weekly or other summary of the same (e.g., a "what I did today" summary). For instance, the application may display hours worked, hours exercised, foods eaten, amount walked, time spent in transit, or the like. Further in some embodiments, an application for a mobile device may determine when a person should go to bed based on scheduled activities the next day (e.g., by accessing the user's calendar on the mobile device), prior lifestyle habits, etc., and provide warnings ahead of and at the appropriate time. For instance, the application (e.g., through an avatar, via alarms, etc.) may warn the user to start winding down an hour before bed, a half an out before bed, shower, etc., and/or provide suggestions for relaxing the user to improve likelihood of a good nights rest. A more intelligent alarm may be created that takes into account how long a user showers or takes to get ready for work based on past behavior of the user.

Accordingly, while the present invention has been disclosed in connection with exemplary embodiments thereof, it should be understood that other embodiments may fall within the spirit and scope of the invention, as defined by the following claims.

The invention claimed is:

1. A system comprising:
a mobile device; and
one or more biometric sensors configured to measure biometric data of a user, the one or more biometric sensors operative to communicate measured biometric data to the mobile device, the mobile device configured to:
collect first information provided by or about the user;
collect second information about the user from the one or more biometric sensors, including at least one of exercise information and sleep information for the user;
determine one or more recommended future, health-related behaviors for the user to perform, the one or more recommended future, health-related behaviors being determined based on the first and second collected information;
communicate at least one of the recommended future, health-related behaviors to the user via an avatar;
generate a reminder to perform the at least one of the recommended future, health-related behaviors, the reminder including an avatar representing an appearance of the user;
display, at a first time, first visual information indicating a skewed life expectancy of the user wherein the first visual information is based on the collected second information; and
display, at a second time, second visual information indicating a readjusted life expectancy of the user, wherein the readjusted life expectancy of the user is based on the collected second information on which the first visual information is based.

2. The system of claim 1 wherein the one or more biometric sensors includes at least two biometric sensors that together are configured to monitor two or more of heart rate, perspiration, and acceleration.

3. The system of claim 1 wherein the first information includes food intake information of the user, and wherein the mobile device is configured to obtain at least one of the one or more recommended future, health-related behaviors for the user to perform based thereon.

4. The system of claim 1 wherein the first information includes travel information for the user and wherein the mobile device is configured to obtain at least one of the one or more recommended future, health-related behaviors for the user to perform based thereon.

5. The system of claim 4 wherein the mobile device is configured to track travel of the user by using GPS.

6. The system of claim 4 wherein the mobile device is configured to track travel of the user by monitoring internet searches performed by the user on the mobile device.

7. The system of claim 1 wherein at least one of the first information and second information includes sleep information of the user, and wherein the mobile device is operative to obtain at least one of the one or more recommended future, health-related behaviors for the user to perform based thereon.

8. The system of claim 1 wherein the first information includes relationship information of the user, and wherein the mobile device is configured to obtain future, health-related behaviors for the user to perform based thereon.

9. The system of claim 8 wherein the mobile device is configured to obtain relationship information of the user from one or more social networking sites.

10. The system of claim 1 wherein the first information includes spending of the user, and wherein the mobile device is configured to obtain at least one of the one or more recommended future, health-related behaviors for the user to perform based thereon.

11. The system of claim 10 wherein the mobile device is configured to track spending of the user by tracking payments made using the mobile device.

12. The system of claim 1 wherein the first information includes information regarding at least one of drinking habits, and smoking habits of the user, and wherein the mobile device is configured to obtain at least one of the one or more recommended future, health-related behaviors for the user to perform based thereon.

13. The system of claim 1 wherein the mobile device is configured to recognize at least one stimulus experienced by the user that is a trigger of the user for engaging in a predetermined habit.

14. The system of claim 13 wherein the mobile device is configured to recognize at least one stimulus experienced by the user that is a trigger of the user for engaging in overeating.

15. The system of claim 13 wherein the mobile device is configured to alert the user of an occurrence of the trigger.

16. The system of claim 1 wherein the mobile device is configured to track stress levels of the user based on measured biometric data and to obtain at least one of the one or more recommended future, health-related behaviors for the user to perform based thereon.

17. The system of claim 1 wherein the mobile device is configured to access a calendar of the user on the mobile device, determine when the user should go to bed based on activities to be performed on a subsequent day and alert the user when to go to bed.

18. The system of claim 1 wherein the mobile device is configured to communicate the recommended future, behavior by causing a calendar of the user on the mobile device to generate one or more reminders that remind the user to perform the behavior.

19. A system comprising:

a mobile device; and one or more biometric sensors configured to measure biometric data of a user, the one or more biometric sensors configured to communicate measured biometric data to the mobile device, the mobile device configured to:

collect information from the mobile device and the one or more biometric sensors, including at least one of exercise information and sleep information of the user;

determine one or more recommended future, health-related behaviors for the user to perform, the one or more recommended future, health-related behaviors based on the collected information; and communicate at least one of the one or more recommended future, health-related behaviors to the user;

access a calendar of the user on the mobile device;

generate one or more reminders that remind the user to perform the at least one of the one or more recommended future, health-related behaviors, the one or more reminders including an avatar representing an appearance of the user;

display, at a first time, first visual information indicating a skewed life expectancy of the user, wherein the first visual information is based on the collected information; and display, at a second time, second visual information indicating a readjusted non-skewed life expectancy of the user, wherein the second visual information is based on the collected information.

20. The system of claim 19 wherein the mobile device is configured to access a calendar of the user on the mobile device, determine when the user should go to bed based on activities to be performed on a subsequent day and alert the user when to go to bed.

* * * * *